United States Patent
Safo et al.

(10) Patent No.: US 7,160,910 B2
(45) Date of Patent: Jan. 9, 2007

(54) ANTI-SICKLING AGENTS

(75) Inventors: Martin K. Safo, Richmond, VA (US); Richmond Danso-Danquah, Richmond, VA (US); Samuel Nokuri, Richmond, VA (US); Faik N. Musayev, Glen Allen, VA (US); Gajanan S. Joshi, Glen Allen, VA (US); James C. Burnett, Richmond, VA (US); Donald J. Abraham, Midlothian, VA (US)

(73) Assignee: Xechem International, Inc., New Brunswick, NJ (US)

( * ) Notice: Subject to any disclaimer, the term of this patent is extended or adjusted under 35 U.S.C. 154(b) by 0 days.

(21) Appl. No.: 10/725,935

(22) Filed: Dec. 3, 2003

(65) Prior Publication Data

US 2004/0157801 A1    Aug. 12, 2004

(51) Int. Cl.
*A61K 31/341* (2006.01)
*A61K 31/381* (2006.01)
*A61K 31/427* (2006.01)

(52) U.S. Cl. .................. 514/365; 514/448; 514/461

(58) Field of Classification Search ................ 514/365, 514/448, 461
See application file for complete search history.

(56) References Cited

U.S. PATENT DOCUMENTS 4,987,132 A    1/1991    Mase
6,300,332 B1   10/2001   Chang et al.

OTHER PUBLICATIONS

Zaugg et al., J. Biol. Chem. (1977), vol. 252, No. 23, pp. 8542-8548.*

* cited by examiner

*Primary Examiner*—Taofiq Solola
(74) *Attorney, Agent, or Firm*—Mishrilal Jain; Michael Whitam

(57) ABSTRACT

The provides compounds for the treatment of sickle-cell disease. In particular, the invention provides 5-membered heterocyclic anti-sickling agents that are highly effective and non-toxic, and methods for their use. The compounds include analogues and derivatives of naturally occurring occurring 5-hydroxymethyl-2-furfuraldehyde, 5-Ethyl-2-furfuraldehyde, 5-Methyl-2-furfuraldehyde, and 2-furfuraldehyde, and prodrug forms of the compound.

6 Claims, 7 Drawing Sheets

ANTI-SICKLING AGENTS

This invention was made using funds from grants from the National Institutes of Health having grant numbers NIH K01HL04367 and NIH R01HL32793. The United States government may have certain rights in this invention.

DESCRIPTION

BACKGROUND OF THE INVENTION

1. Field of the Invention

The invention generally relates to agents for the treatment of sickle-cell disease. In particular, the invention provides 5-membered heterocyclic anti-sickling agents that are highly effective and non-toxic, and methods for their use.

2. Background of the Invention

Sickle cell disease is one of the most prevalent hematologic genetic disorders in the world (Ingram, 1956; Pauling, et al. 1949) that occurs as a result of a single point mutation of Glu6 in Hb to Val6 in sickle hemoglobin (HbS). Two quaternary structures are known for Hb, the deoxy conformation (tense), and the oxygenated conformation (relaxed). When the allosteric equilibrium is shifted toward the relaxed state, a high-affinity Hb is obtained that readily binds and holds oxygen, while the converse is true for the tense state. Perutz (1970) and Baldwin & Chothia (1979) elucidated at atomic resolution the tetrameric structures of the tense (T) and relaxed (R) forms of Hb. The tetramer is composed of two $\alpha\beta$ dimers that are arranged around a twofold axis of symmetry. This arrangement yields a central water cavity, with two openings; the $\alpha$- and $\beta$-clefts. The source of the tension in the T state is due to crosslinking salt bridges and hydrogen bonds between the subunits, as well as preferential binding of an indigenous allosteric effector of Hb, 2,3-diphosphoglycerate (2,3-DPG) that stabilize the T state by forming salt bridges between the two $\beta$-subunits (Arnone, 1992). The T-R transition occurs as a result of uptake of oxygen which leads to the disruption of many of the T state intersubunit interactions, as well as expulsion of the 2,3-DPG. The allosteric transition results in a rotation of the $\alpha 1\beta 1$ dimer relative to the $\alpha 2\beta 2$ dimer by 12–15° (Baldwin & Chothia, 1979). The R state structure has a smaller central water cavity, as well as fewer intersubunit salt bridges and hydrogen bonds. For a long period of time, the allosteric equilibrium of Hb embodied in the two-state MWC model (Monod, et. al., 1965) was believed to involve only the T-R transition, and the R state quaternary structure was thought to be the only relaxed conformer. However, recent crystallographic and other studies have revealed the existence of multi relaxed Hb states, including R2 and others that exist in solution with R (Silva, et al. 1992; Smith, et al., 1991; Mueser, et al., 2000). There is still a controversy about the physiological importance of all these relaxed states, and how they relate to one another in Hb allostery. Silva et al., (1992) and Smith et al., (1991) suggested that the R2 quaternary structure is an intermediate between the T and R structures. Further analysis has shown that R2 is not an intermediate in the T to R transition, but rather, it is another relaxed end-state structure (Janin & Wodak, 1993; Doyle, et al., 1992). Srinivasan & Rose (1994) have further suggested that R2 may be the physiologically relevant end state and that the R structure is an intermediate structure trapped between the R2 and T states by the high-salt crystallization conditions. In contrast, the R2 structure formation is believed to be favored by low-salt that mimic in vivo condition (Silva et al., 1992; Srinivasan & Rose, 1994).

Hb and HbS have almost identical positions for all amino acids, even in the A helix of the chains where the mutation occurs. The presence of the Val6 results in hydrophobic interaction between the mutation region of one Hb molecule and a region defined by Phe85 and Leu88 in the heme pocket of another Hb molecule. This interaction occurs only in the deoxygenated HbS (deoxyHbS), and induces polymerization of the deoxyHbS molecules into fibers. The formation of HbS polymers causes the normally flexible red blood cells to adopt rigid, sickle like shapes that block small capillaries and cause both local tissue damage and severe pain. The disease is also characterized by other symptoms, including hemolysis, which gives rise to anemia and jaundice, elevation of bilirubin level leading to high incidence of gall stones and impairment of hepatic excretory function. Other clinical features include leg ulceration, pneumonia, enlarged liver and spleen. Other studies on the gellation of deoxyHbS and various Hb variants have also provided crucial information on other contact points on the Hb that are important in stabilizing the HbS fibre (Adachi & Asakura, 1980; Bunn, et al., 1986). There are various therapeutic strategies to treat sickle cell disease (SCD), including (1) *Pharmacological modulation of fetal hemoglobin (HbF)*: HbF has been shown to decrease HbS polymerization, and there are several agents that are known to induce HbF formation by possibly reactivating the genetic switch for HbF (Olivieri & Weatherall, 1998). Examples of such agents include 5-azacytidine, hydroxyurea and cytosine arabinoside (Mehanna, 2001). Unfortunately, there are serious toxic side effects associated with this therapy as a result of high doses and frequency of administration (Edelstein, 1985), (2) *Bone marrow transplantation*: Bone marrow transplant has also been used as a total gene replacement therapy for HbS in extreme cases (Hillery, 1998, Johnson, 1985). This approach is very expensive and has its own inherent toxicities and risks (Hillery, 1998), (3) *Blood transfusion*: This is one of the most common SCD therapies, however, repeated blood transfusions are known to be associated with the risks of infectious diseases, iron overload and allergic reactions (Ballas, 1999), (4) *Opioid analgesics*: This therapy is necessary to deal with pain crisis, however, opioid therapy often results in addiction and/or seizures and/or depression, (Ballas, 1999), (5) *Erythrocyte membrane acting agents*: Since the sickling process is partly dependent on intracellular concentration of sickle Hb, agents that induce cell swelling (Asakura, 1980) or inhibit cell dehydration (Orringer & Berkwitz, 1986) could decrease the HbS concentration and help delay the polymerization process, and (6) *Antigelling agent or HbS modifiers*: These compounds interfere with the mechanism of polymerization by either binding directly to or near contact site(s) of the deoxyHbS to inhibit the polymerization process or act directly on HbS to shift the allosteric equilibrium to the more soluble high-affinity HbS.

In blood, Hb is in equilibrium between the T and the relaxed states. The Hb delivers oxygen via an allosteric mechanism, and the ability for the Hb to release or take oxygen can be regulated by allosteric effectors. The allosteric equilibrium between the T and relaxed states (FIG. 1) shows a typical oxygen equilibrium curve (OEC) for Hb, i.e. a plot of the percentage of oxygen bound by Hb against the partial pressure of oxygen. When the allosteric equilibrium is shifted towards the relaxed state (left shift of the curve), a high-affinity Hb is obtained that more readily binds and holds oxygen while a shift toward the T state (right shift of the curve) results in a low-affinity Hb that more easily releases oxygen. An increase in the naturally occurring allosteric effector, 2,3-DPG in red cells right shifts the OEC as does an increase in temperature and decrease in pH (Reeves, 1980). An increase in pH and lowering of the temperature and DPG levels left shifts the OEC. The degree of shift in the OEC is reported as an increase or decrease in $P_{50}$ (partial pressure of oxygen at 50% Hb saturation). Regulating the allosteric equilibrium to the relaxed conformation has been of been of interest in medicine, In particular, the identification of non-toxic compounds that efficiently bind to HbS and produce high-affinity HbS which does not polymerize have been clinically evaluated as antisickling agents to treat SCD. There is an ongoing need to identify such compounds to be used as antisickling agents to treat sickle cell anemia. See, for example, the use of vanillin (Abraham, 1991), 12C79 (Fitzharris, 1985), furfural (Zaugg, et al., 1997), and substituted isothiocyanates (Park, et al. 2003).

SUMMARY OF THE INVENTION

The present invention provides compounds that are highly effective, specific and non-toxic anti-sickling agents, as well as prodrug forms of the compounds. The compounds are based on naturally occurring 5-hydroxymethyl-2-furfuraldehyde (5HMF or AMS-13), 5-Ethyl-2-furfuraldehyde (5EF), 5-Methyl-2-furfuraldehyde (5MF) and 2-furfuraldehyde (FUF), and include analogues and derivatives of these compounds. Methods for using the compounds to treat sickle cell disease are also provided.

It is an object of this invention to provide a method for treating sickle cell disease in a patient in need thereof. The method comprises the step of administering to the patient one or more compounds of the formula:

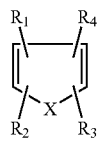

where R1 is CHO, or an aldehyde protecting group; R2, R3 and R4 are the same or different and are H, OH, alkyl, alkoxy, hydroxy-alkyl, halogen, aryl or O-aryl; and X=NH, O, S, Se or P. The compound is administered in sufficient quantity to ameliorate symptoms of sickle cell disease. In one embodiment of the invention, R1 is CHO; R5 is H, alkyl or aryl; and m=1–6; and the compound is selected from the group consisting of

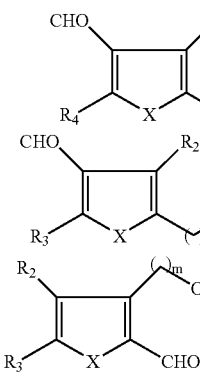 and 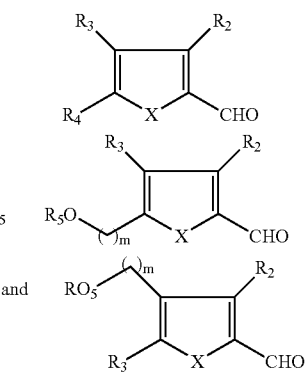

In another embodiment of the invention, R1 is a heterocyclic ring aldehyde protecting group; R6 and R7=H or alkyl and may be the same or different; and n=0–4; and the compound is selected from the group consisting of

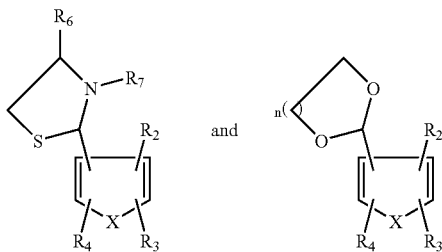

Examples of the compound within this group include the following (wherein in some of the examples R8 and R9 can be the same or different and are H, alkyl or aryl)

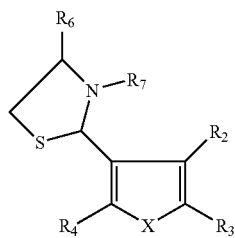

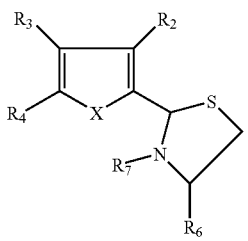

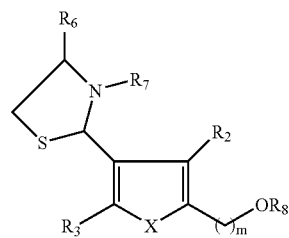

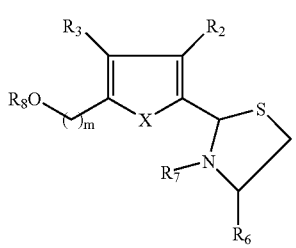

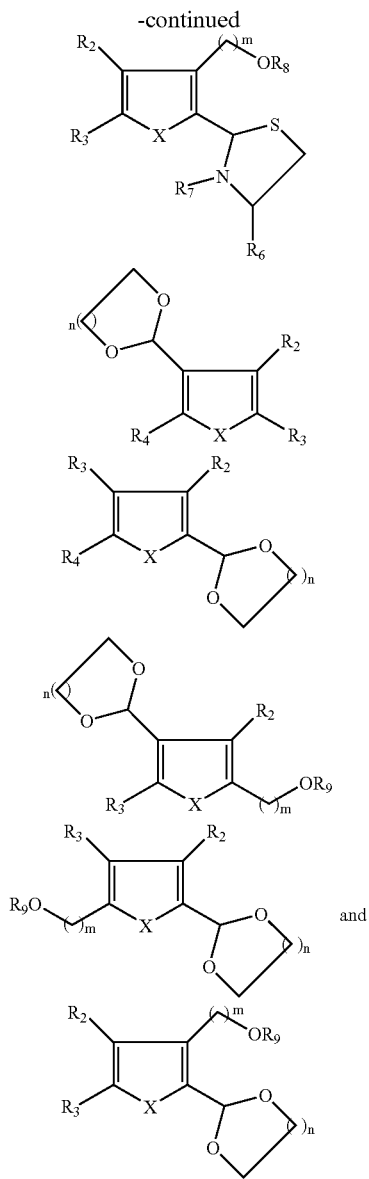

In preferred embodiments of the invention, the compound is selected from the group consisting of

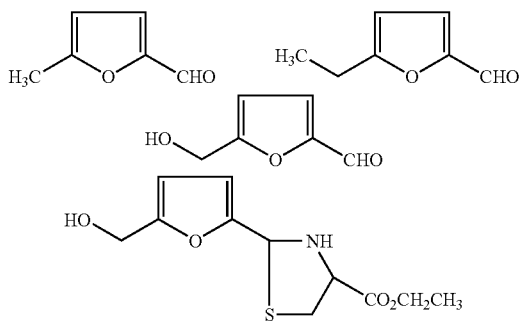

The invention also contemplates the use of the compounds of the general formula:

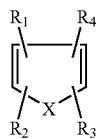

where R1 is CHO, or an aldehyde protecting group, R2, R3 and R4 are the same or different and are H, OH, alkyl, alkyoxy, hydroxy-alkyl, halogen, aryl or O-aryl; and X=NH, O, S, Se, or P to treat symptoms of patients suffering sickle cell anemia including particularly jaundice and elevated levels of bilirubin. A sufficient quantity of one or more of the compounds of the above general formula is administered to ameliorate or reduce jaundice or levels of bilirubin, respectively.

The invention also contemplates the use of the compounds of the general formula:

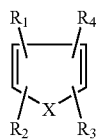

where R1 is CHO, or an aldehyde protecting group, R2, R3 and R4 are the same or different and are H, OH, alkyl, alkyoxy, hydroxy-alkyl, halogen, aryl or O-aryl; and X=NH, O, S, Se, or P in the treatment of patients with cancer. One or more of the compounds would be administered to a patient in a quantity sufficient to change the oxygen carrying capacity of the blood to a state beneficial to eradicating the cancer. In addition, similar to the methods described in U.S. Pat. No. 5,705,521 to Abraham, which is herein incorporated by reference, the compounds of this invention can be administered to a patient that is or is going to undergo radiation therapy to assist in the effectiveness of the radiation to destroy the cancer.

DETAILED DESCRIPTION OF THE PREFERRED EMBODIMENTS OF THE INVENTION

Figure 1:
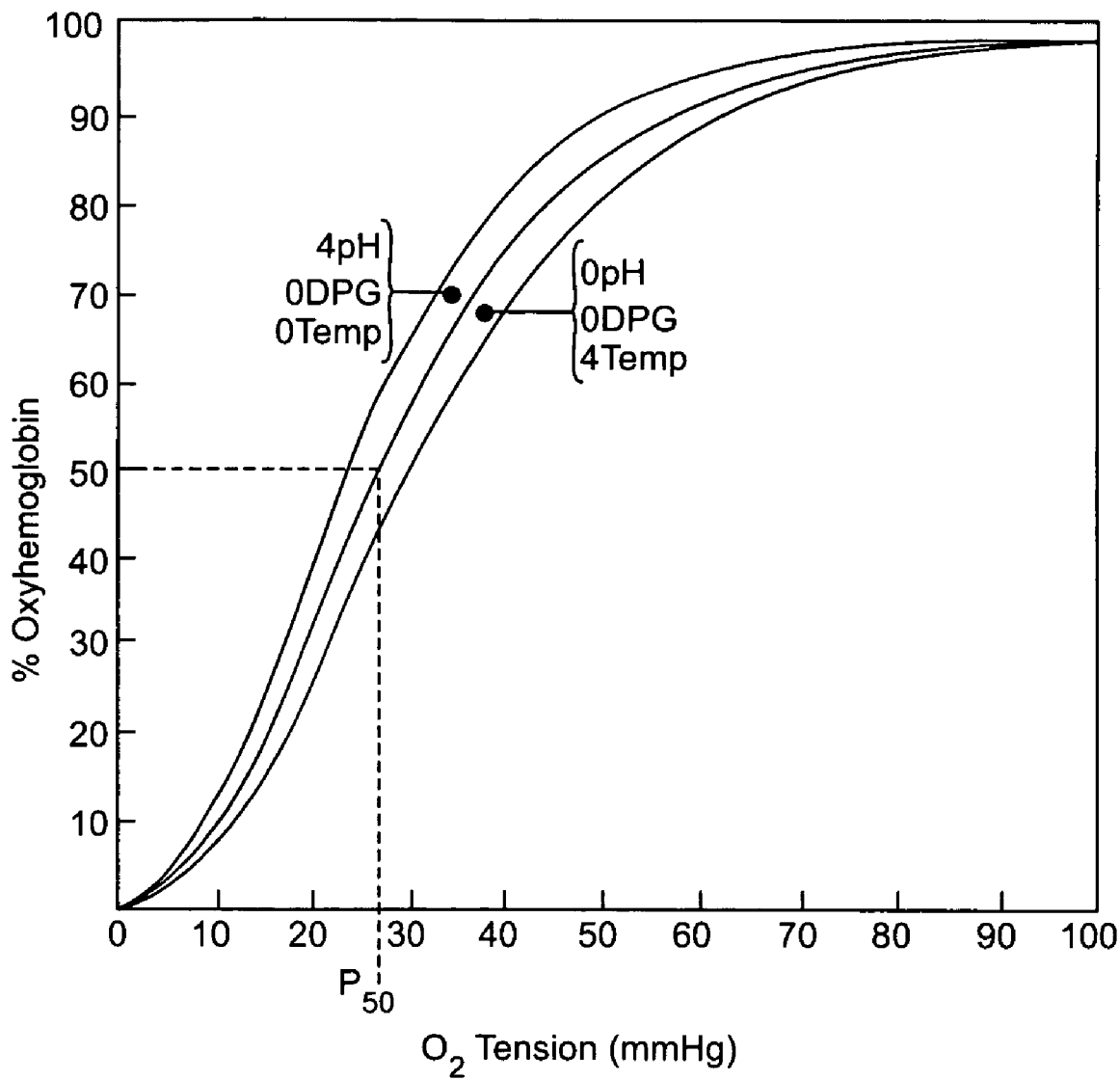
FIG. 1. The effects of temperature, pH, and DPG levels on the Hb oxygen equilibrium curve.

The present invention provides antisickling agents. The agents are 5-membered heterocyclic compounds that are based on the naturally occurring substances 5HMF, 5EF, 5MF and FUF. The compounds include analogues and derivatives of 5HMF, 5EF, 5MF and FUF. By "analogue" and "derivative" we mean compounds that possess the same basic structure as the parent molecule, but in which the various R groups as depicted in the Formulas below are replaced as indicated in the descriptions of the formulas.

The compounds of the present invention exhibit high antisickling activity, specificity, and very low toxicity. The compounds contain a central ring moiety and are of general Formula 1

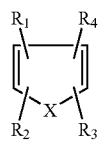

Formula 1 where R1 is CHO, or an aldehyde protecting group that leaves the central ring moiety and allows the central ring moiety to revert to an aldehyde in the body (heterocyclic ring moieties being preferred); R2, R3 and R4 are the same or different and are H, OH, alkyl, alkoxy, hydroxy-alkyl, halogen, aryl and O-aryl; and X=NH, O, S, Se, and P.

Preferred embodiments of the compounds are given in Formulas 2–7 below, where R1 is shown as CHO, where R2–R4 are shown and are moieties as set forth above, and, with respect to formulas 4 and 5, where R4 is an alkoxy or hydroxy-alkyl; R5=H, alkyl, or aryl, and m=1–6.

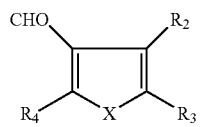

Formula 2

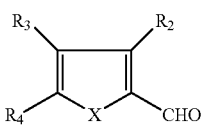

Formula 3

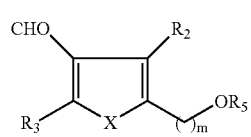

Formula 4

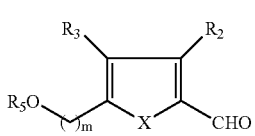

Formula 5

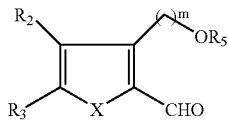

Formula 6

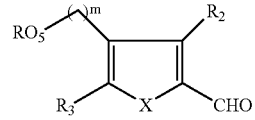

Formula 7

In preferred embodiments of the invention, the antisickling compounds are those of Formula 5 where m=1–6 and R5 is hydrogen.

The invention further provides prodrugs of these compounds. By "prodrug" we mean a form of the compound that contains at least one "protective" chemical group, the presence of which protects the aldehyde moiety of the compound against metabolism/degradation until the prodrug is in an environment appropriate for removal of the protecting group(s) and "release" of the active form of the compound. The overall effect of the protecting group is to increase the bioavailability of the active aldehydic compound once the compound reverts to the aldehyde. One preferred generic prodrug of the compounds of the present invention is represented in Formula 8:

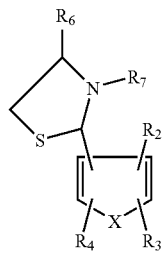

Formula 8

Where R2, R3 and R4 are the same or different and can be H, OH, alkyl, alkoxy, hydroxylkyl, halogen, aryl or O-aryl; R6=H or alkyl; R7=H or alkyl; and X=NH, O, S, Se, or P. Use of protecting groups of this type, (e.g. the amino acids cysteine and homocysteine) have the advantage of resulting in the release of a non-toxic amino acid upon removal of the protecting group. It should be understood that other aldehyde protecting groups may be used in the practice of this invention. Protection groups of this type are taught, for example, in U.S. Pat. No. 6,251,927 to Lai et al., (Jun. 6, 2001) the complete contents of which are hereby incorporated by reference. These include, but are not limited to conversion of the aldehyde to the corresponding imine, alcohol, acetal, ester, macrcocyclic ester/acetal, macrocyclic ester/imine, hemiacetal, and the like.

Preferred variations of this type of compound are given in Formulas 9–13:

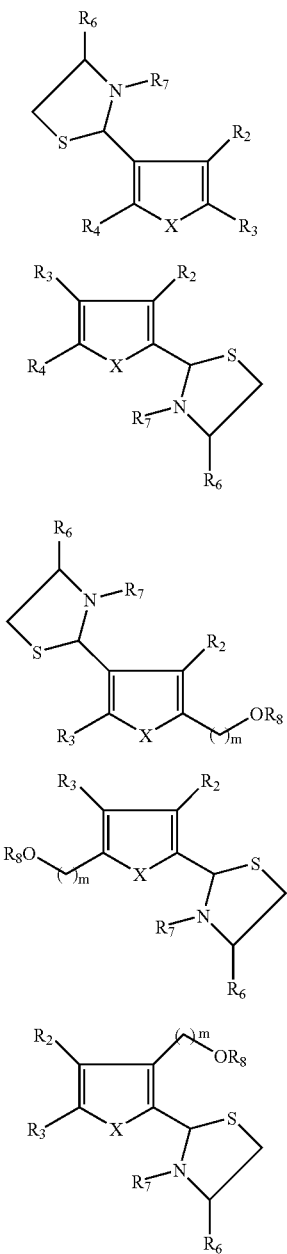

Formula 9

Formula 10

Formula 11

Formula 12

Formula 13 where R8=H, alkyl or aryl and m=1–6.

A second preferred generic prodrug of the compounds of the present invention is shown in Formula 14

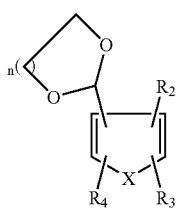

Formula 14 where R2, R3 and R4 are the same or different and can be H, OH, alkyl, alkoxy, hydroxylkyl, halogen, aryl or O-aryl; X=NH, O, S, Se, or P; and n=0–4. These prodrugs have the advantage of being made in a relatively facile manner, but do not have the advantage of producing a natural product upon release from the prodrug. Variations of this type of prodrug are given in Formulas 15–19,

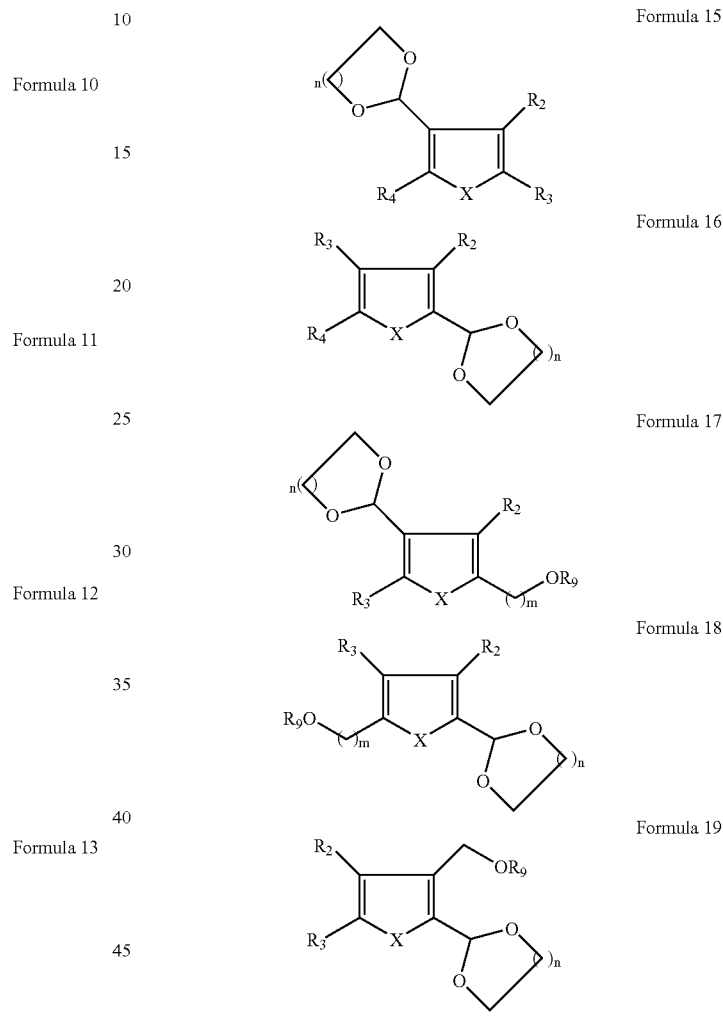

Formula 15

Formula 16

Formula 17

Formula 18

Formula 19 where R9=H, alkyl, or aryl and m=1–6.

The present invention also provides a method for treating sickle cell disease, and to treat symptoms of sickle cell disease such as jaundice and elevated levels of bilirubin. The method involves administering to a patient with sickle cell disease a quantity of at least one compound of the present invention sufficient to ameliorate or reduce symptoms of the disease, e.g. to decrease or eliminate jaundice and elevated bilirubin. The compounds may be administered as the compounds themselves, or in the form of a prodrug.

The compounds of the present invention are potent antisickling agents. Those of skill in the art will recognize that the amount of such an agent that is to be given to a patient will vary depending on several factors, including but not limited to blood volume, hematocrit, patient age, gender, weight, overall physical health, presence of other disease conditions, the particular compound being administered, and the like. However, the amount will generally be in the range of from about 50 to about 1000 mg/kg and more preferably in the range of from about 100 to about 750 mg/kg. For example, an adult sickle cell patient with a blood volume of 4 L and 25% hematocrit will need about 378–630 mg/kg of the most potent compound, 5HMF, and more preferably the dose will be in the range from 200–630 mg/kg.

The compounds of the present invention may be administered in any form that is suitable for delivering an active amount of the compound to the patient being treated. For examples, the compound may be administered as solid pills or capsules, liquids for oral administration, injectable formulations, etc. The compounds may be provided alone or in combination with other constituents, and may be provide in pure or salt form (e.g., organic or inorganic salts, etc.). In addition, the compounds may be formulated with carriers such as aqueous or oil based vehicles, and can be accompanied by preservatives (e.g., methyl paraben or benzyl alkonium chloride (BAK)), surfactants (e.g. oleic acid), solvents, elixirs, flavoring agents (in the case of oral delivery), starch, and other materials (preferably those which are generally regarded as safe (GRAS)). In a preferred embodiment, the compound will be administered as a preparation for oral administration in an alcohol-based or aqueous-based carrier.

Likewise, the method of administration may be any of a wide variety of methods that are well known to those of skill in the art, such as intravenous, intradermal injection, subcutaneous injection, intramuscular injection, intraperitoneal injection; oral, rectal and buccal delivery; transdermal delivery; inhalation; etc. In a preferred embodiment, the method of administration is oral delivery. Further, the compounds of the present invention may be administered in conjunction with other known sickle cell disease treatments, or treatments for other related or unrelated disease conditions (e.g. treatment for anemia), and with other beneficial ancillary regimens such as dietary supplements, exercise regimens, and the like.

While a primary use of the anti-sickling agents of the present invention is to treat sickle cell disease, those of skill in the art will recognize that the agents may be used in other applications for which it is beneficial to cause destabilization of the tense (T) states of hemoglobin, and the switching of the allosteric equilibrium in favor of the high-affinity Hb in the form of the R2-state Hb. This aspect of the invention is further illustrated in Example 5 below. For example, the invention also contemplates the use of the compounds in the treatment of patients with cancer. One or more of the compounds would be administered to a patient in a quantity sufficient to change the oxygen carrying capacity of the blood to a state beneficial to eradicating the cancer. In addition, similar to the methods described in U.S. Pat. No. 5,705,521 to Abraham, which is herein incorporated by reference, the compounds of this invention can be administered to a patient that is or is going to undergo radiation therapy to assist in the effectiveness of the radiation to destroy the cancer.

The compounds may also be used for research purposes. In particular, the generic compounds may serve as parent structures for rational drug design of additional derivatives and analogues. Examples include but are not limited to other forms of the compounds that are more or less active, or more or less stable; that have altered solubility properties; or that have moieties that serve to target the compounds to a desired location, e.g. across the cell membrane. Alternatively, the compounds provided here may serve as parent structures for the design of other forms of prodrugs.

Some of the compounds used in the practice of the present invention are naturally occurring, for example, 5-Hydroxymethyl-2-furfuraldehyde (5HMF or AMS-13), 5-Ethyl-2-furfuraldehyde (5EF), and 5-Methyl-2-furfuraldehyde (5MF) (see FIG. 2). 5HMF is present in many foods such as sweet potatoes, fruits, honey, milk, beer, tomato products, cigarette smoke, and coffee, where the concentration sometimes exceeds 6 g/kg. Commercially, 5HMF is prepared from the fructose portion of sugar.

Methods for synthesizing the prodrug compounds of the present invention are also described herein, with exemplary synthesis schemes being given in Example 4 below. Such organic synthesis methods of protecting aldehydes are well-known to those of skill in the art.

EXAMPLES

Example 1

Figure 2:
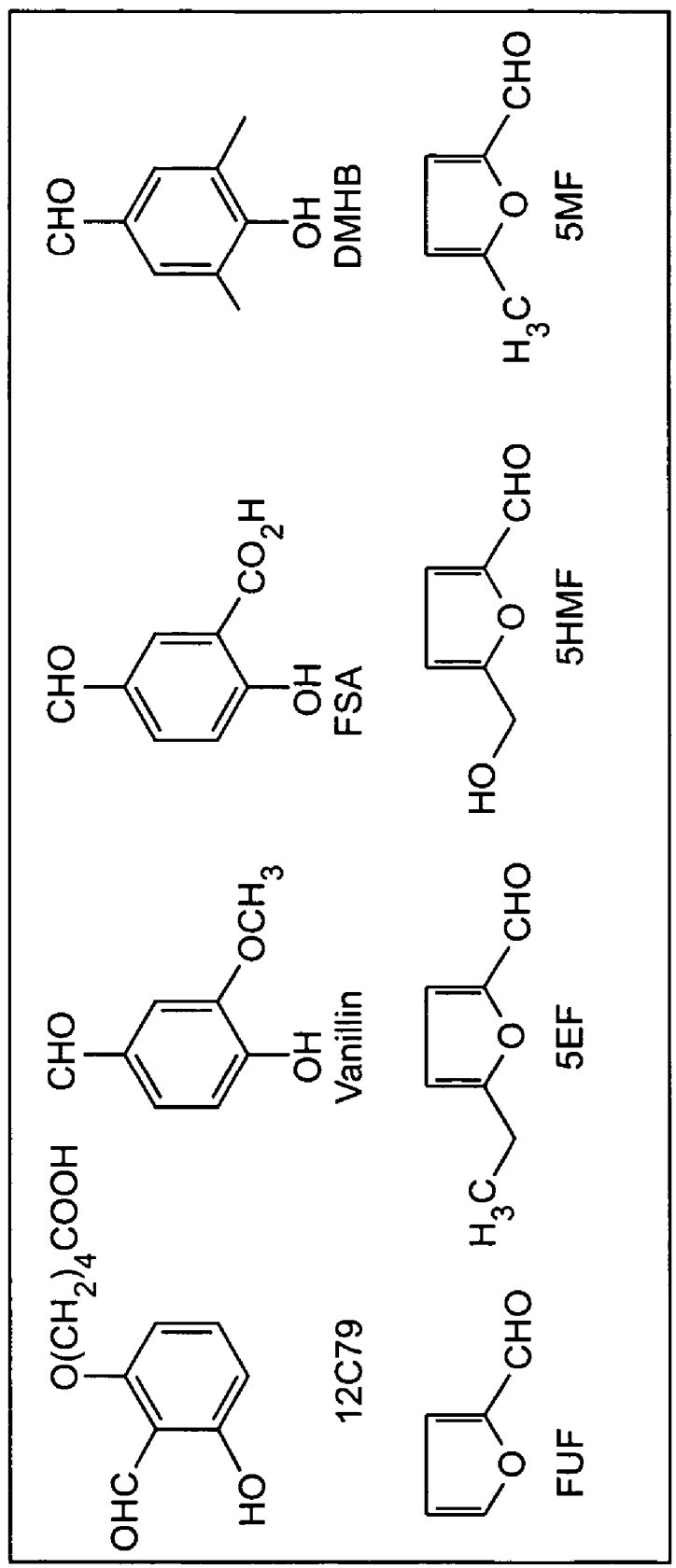
FIG. 2. Structures of some furanic as well as other compounds discussed in the application.

Structural Basis for the Potent Antisickling Effect of a Novel Class of 5-Membered Heterocyclic Aldehydic Compounds: In Vitro Tests and X-ray Crystallographic Studies of the Furanic Compounds, 5HMF, 5MF, 5EF and FUF Chemical structures of 5HMF, 5MF, 5EF and FUF are shown in FIG. 2.

Regulating the Hb allosteric equilibrium to the relaxed conformation has been of interest in medicine, as compounds that bind to HbS that produce high-affinity HbS, which do not polymerize have been clinically evaluated as antisickling agents to treat sickle cell anemia. Two such compounds are vanillin (Abraham, et al., 1991) and 12C79 (Beddell, et al., 1984; Fitzharris, et al., 1985; Orringer, et al., 1986). Both compounds are aldehydes and form Schiff base adducts with Hb. Clinical studies with 12C79 (FIG. 2) showed that intravenous infusion of this compound (40 mg/kg) in patients with SCD resulted in the formation of compound-Hb adducts at levels of more than 30% without any adverse effect (Orringer, et al., 1988). Vanillin (FIG. 2) is a food flavoring compound, and because it is relatively non-toxic, makes it a very attractive therapeutic agent for SCD. A low-resolution structure of T state Hb complexed with vanillin showed that the compound binds to two different sites: a primary site near His103, Cys104 and Gln131, and a secondary site between His116 and His117 (Abraham, et al., 1991). Based on the results of the X-ray crystallographic analysis and functional studies, Abraham, et al., (1991) suggested that vanillin acts to decrease the polymerization of HbS by shifting the allosteric equilibrium toward the high-affinity HbS molecule in the form of R state; as well as stereospecific inhibition of the polymerization of T state HbS. Additional studies of several analogs of vanillin by Abraham, et al., (1995) and Boyiri, et al., (1995) showed that these compounds, unlike vanillin, bind to the N-terminal Val1 of T state Hb, and surprisingly effect opposite shifts in the OEC. Agents such as, 5-formylsalicylic acid (FSA, FIG. 2), which form Schiff base interactions with the N-terminal Val1 nitrogen, and provide groups for both salt bridge and hydrogen bonding with the opposite dimer (across the Hb two-fold axis), shift the OEC toward the right. In contrast, agents such as, 3,5-dimethyl-4-hydroxybenzaldehyde (DMHB, FIG. 2), which also bind to the N-terminal Val residue of T state Hb in a similar fashion as FSA without any salt bridge interactions with the opposite dimer, shift the OEC toward the left.

In the current studies, we combined the use of aldehydic covalent modifiers of Hb with our knowledge of the molecular regulation of the allosteric equilibrium to produce potent antisickling compounds that should be clinically safe. Specifically, we examined 5-hydoxymethyl-2-furfural (5HMF) and several of its analogs, including furfural (FUF), 5-methyl-2-furfural (5MF) and 5-ethyl-2-furfural (5EF) (all shown in FIG. 2) for their antisickling potencies. These compounds were found to significantly shift the allosteric equilibrium to the high-affinity Hb, and also act as potent inhibitors of homozygous sickle red blood (SS) cell sickling. One of the compounds, 5HMF modifies HbS by 70% compared to 15% for vanillin. 5HMF also inhibits in vitro SS cell sickling by 90%, four times more than vanillin. Also, in vivo antisickling studies using sickle cell transgenic (tg) mice show 5HMF to prolong the life of the hypoxic mice about four times longer compared to control. 5HMF is found in everyday food, and has $LD_{50}$ of 2.5–5.0 g/Kg (US EPA, 1992) compared to 1.58 for vanillin. Thus we now have a compound which is safe, more potent than any known aldehydic antisickling agent, able to transverse red blood cell to react and modify HbS. In addition, 5HMF makes an ideal scaffold upon which to build more potent and safe compounds.

X-ray crystallographic studies of Hb complexed with these compounds indicate that they form Schiff base adducts in a symmetrical fashion with the N-terminal αVal1 nitrogens of Hb. Remarkably, two co-crystal types were isolated during these experiments: one crystal type was found to be composed of the low-affinity or tense (T) state Hb quaternary structure in complex with the compounds; the other crystal type was composed of high-affinity or relaxed state Hb (with a R2 quaternary structure) in complex with the compounds. Furthermore, the examined heterocyclic aldehydes were found to bind strongly to the R2 state, but weakly to the T state. Crystallization of the same compounds with liganded Hb resulted in only relaxed R state crystals, which also indicated weak compound binding. These results suggest that the examined heterocyclic aldehydes prevent polymerization of sickle hemoglobin (HbS) and inhibit the sickling of SS cells by stabilizing HbS in the high-affinity R2 state. Comparing the high resolution crystal structures of 5HMF and vanillin bound to Hb, shows 5HMF to bind much stronger, an indication that 5HMF may reside longer at the binding site. This explains why 5HMF is many fold potent than vanillin. Most importantly the stronger binding of 5HMF to Hb may translate into an even longer half-life and increased bioavailability for 5HMF compared to vanillin, with a concomitant decrease in the dosage needed for therapy. The biological, as well as the crystallographic studies of the furanic compounds reveal for the first time the exact molecular mechanism for the antisickling effects of covalently modifying aldehydes that bind to N-terminal αVal1 nitrogens of Hb. These examined compounds also represent a new class of potentially therapeutic agents for treating sickle cell disease (SCD).

Experimental Procedure

Materials and General Procedures. The following compounds: vanillin, FUF, 5MF, 5EF and 5HMF were purchased from Aldrich Chemical Company. Normal red blood (AA) cells were collected from adult donors. SS cells were obtained from patients with SCD. Purified human adult Hb in 50 mM Bis Tris buffer, pH 6.8, was prepared from discarded human blood as previously described (Safo and Abraham, 2003).

Oxygen Equilibrium Studies with Normal Whole Blood. Normal blood samples (hematocrit 40%) in the presence of 5 mM Vanillin, FUF, 5MF, 5EF and 5HMF (solubilized in DMSO) were equilibrated at 37° C. for 1 hr. The samples were then incubated in IL 237 tonometers (Instrumentation Laboratories, Inc. Lexington, Mass.) for approximately 10 min at 37° C., and allowed to equilibrate at oxygen tensions 7, 20, and 60 mmHg. The samples were aspirated into an IL 1420 Automated Blood Gas Analyzer and an IL 482 or IL 682 Co-oximeter (Instrumentation Laboratories) to determine the pH, $pCO_2$, $pO_2$ and the Hb oxygen saturation values ($sO_2$). The $pO_2$ and $sO_2$ values at each oxygen saturation level were then subjected to a non-linear regression analysis using the program Scientist (Micromath, Salt Lake City, Utah) to calculate the $P_{50}$ and Hill coefficient values ($n_{50}$). $P_{50}$ is the oxygen pressure in mmHg at which Hb is 50% saturated with oxygen. A dose-response study with 5HMF was performed at final compound concentrations of 1 and 2 mM.

Oxygen Equilibrium Studies with Homozygous Sickle Red Blood Cells. SS cells were suspended in PBS to a final hematocrit of 10%. Vanillin, FUF, 5HMF (solubilized in DMSO) was added to this suspension at final concentrations of 5 mM and incubated at 37° C. for 1 hr. A 40 uL aliquot of this suspension was added to 4 ml Hemox buffer and subjected to oxygen equilibrium analysis (37° C.) using a Hemox-Analyzer (TCS Scientific Corp., Southampton, Pa.) (Asakura, 1979).

Transport through Homozygous Sickle Red Blood Cell Membrane and Reaction with HbS. The compound-treated SS cells obtained in the preceding experiment (oxygen equilibrium studies with SS cells) were hemolyzed by adding 5 volumes of 5 mM potassium phosphate buffer, pH 7.4 containing 0.5 mM EDTA. After centrifugation, the hemolysate was subjected to both oxygen equilibrium analysis using Hemox-Analyzer and cation-exchange HPLC analysis using a Hitachi HPLC apparatus (Model D-7000 Series) and a Swift™ WCX column (Swift™ WCX-PEEK: 50 mm×4.6 mm, Isco, Inc., Lincoln, Nebr.). The column was developed using a linear gradient of phase B from 25% to 90% at 410 nm (Mobile Phase A: 40 mM Bis-Tris, 5 mM EDTA, pH 6.5; Phase B: 40 mM Bis-Tris, 5 mM EDTA, 0.2 M sodium chloride, pH 6.5). The HbS adduct formation (modification of HbS) values are expressed in percentages, using the following formula:

$$Mod\ HbS\ (\%) = \frac{\text{peak area of modified } Hb}{(\text{peak area of modified } Hb + \text{peak area of unmodified } Hb)} \times 100$$

Antisickling Studies with Homozygous Sickle Red Blood Cells. The effects of vanillin, FUF and 5HMF on the inhibition of SS cells sickling were evaluated as previously described (Asakura & Mayberry, 1984). Briefly, SS cells suspended in buffered saline solution, pH 7.4 (hematocrit of 10%) were incubated at 37° C. with 4% oxygen in the presence of 5 mM compound. Aliquots (10 ul) of the suspensions were obtained after 5 hrs and fixed with 2% glutaraldehyde solution without exposure to air. Morphological analysis and percentage of SS cells that were not sickled were conducted using a computer-assisted image analysis system as described elsewhere (Hijiya, 1991). Dose-response studies of FUF and 5HMF at compound concentrations of 1 and 2 mM were also performed.

The Effect of Compounds on Homozygous Sickle Red Blood Cell Size. To study the effect of the compounds on the degree of hydration/dehydration of SS cells, the compound-treated SS cells obtained in the preceding experiment (anti-sickling studies with SS cells) were evaluated with a Hemavet Cell Analyzer to determine the mean corpuscular volume (MCV).

Crystallization Experiments. Crystallization experiments to obtain T and R state crystals were conducted with FUF and 5HMF. The experiments involved 4–25 molar excess of the compounds to Hb (tetramer). For the T state crystallization experiment, the compounds solubilized in DMSO were incubated with deoxy Hb (60 mg/mL protein) for at least 1 hour to form the Schiff base adduct. Sodium cyanoborohydride, in 4–25 molar excess of Hb, was added to reduce the reversible Schiff base-adduct to the corresponding alkylamine covalent bond. Subsequent crystallization of the compound-deoxy Hb complex solutions in 10 mL test tubes using 3.2–3.6 M sulfate/phosphate precipitant (pH 6.5) was performed in a glove box under nitrogen atmosphere as previously described (Safo, et al., 2003; Perutz, 1968) for obtaining high-salt T state crystals. Reduction of the Schiff base-adduct is necessary to observe the bound compound crystallographically (Boyiri, et al., 1995). Unexpectedly, the experiment resulted in two different crystals—a rectangular crystal (space group $P2_1$), which is isomorphous to T state native crystal, and a trigonal crystal (space group $P3_221$), which was later determined to have a relaxed state conformation in the form of R2 quaternary structure. The T state crystals grew between 2–10 days, while the R2 state crystals grew between 7–30 days.

Another experiment was designed to crystallize the compound-Hb complexes in R state form using carbonmonoxy Hb (COHb), following a previously described procedure (Safo, et al., 2003; Perutz, 1968). Oxygenated Hb solution was evacuated for about 10 minutes, and the resulting deoxy Hb solution was fully saturated with CO to generate COHb. The compounds solubilized in DMSO were then reacted with the COHb, followed by addition of sodium cyanoborohydride to reduce the Schiff base-adduct. Crystallization was carried out with a solution of 30–50 mg/mL protein, 3.2–3.4 M $Na^+/K^+$ phosphate, pH 6.4, and two drops of toluene in 10 ml test tubes. The experimental procedures were done under aerobic condition, and resulted in co-crystals (4–30 days) isomorphous to R state native crystals (space group $P4_12_12_1$).

Data Collection, Processing and Structure Refinement. X-ray diffraction data sets for the R, R2 and T state co-crystals were collected at 100° K using a Molecular Structure Corporation (MSC) X-Stream Cryogenic Cooler System (MSC, The Woodlands, Tex.), a R-Axis II image plate detector equipped with OSMIC mirrors, and a Rigaku RU-200 generator operating at 50 kV and 100 mA. Prior to use in diffraction, the crystals were first washed in a cryoprotectant solution containing 50 µL mother liquor and 10–12 µL glycerol. The data sets were processed with MSC BIOTEX software program. All structure refinements and omit maps were performed with the CNS program (Brunger, et. al., 1998). Model building and correction were carried out using the graphic program TOM (Cambillau & Horjales, 1987).

Structure Determinations and Refinements of the R2 State Complex Structures. The structure of the FUF-Hb complex in the R2 state crystal was the first to be determined by molecular replacement method (Navaza, 1994) using the $\alpha1\beta1-\alpha2\beta2$ R2 state native Hb structure (PDB code 1BBB) as a search model. The translation function using the space group $P3_221$ gave a solution of a tetramer in the asymmetric unit with a final correlation coefficient of 69.2 and Rfactor of 35.5% for data between 8.0–4.0 Å. Prior to using the R2 structure as a search model, we assumed the crystal to be a T state Hb in another crystal form. However, the use of a T state structure (PDB code 2HHB) as a search model failed to give a clear solution. A similar search with a R state structure (PDB code 1AJ9) also failed to give a clear solution. The molecular replacement model was subjected to a rigid body refinement, followed by conjugate gradient minimization and simulated annealing. Strong and clear densities were identified for two FUF molecules bound at the N-terminal αVal1 residues in a symmetry-related fashion. The N-terminal αVal1 binding site is located in the central water cavity of Hb close to the mouth of the α-cleft. The electron density from the bound compound overlapped that of the αVal1 nitrogen, suggesting a covalent interaction between FUF and the nitrogen. The electron density map also showed ligation of the four heme Fe atoms, and water ligands were fitted to the density. Alternate fitting of $O_2$ ligands produced distorted geometry of the Fe—O—O bonds and angle. Several alternate rounds of conjugate gradient minimization, simulated annealing, individual B factor refinements, and the addition of 7 sulfate anions and 297 water molecules, with manual model corrections, brought the final Rfactor to 21.7% and Rfree to 27.4% at 2.25 Å resolution. The crystallographic data for the structure is summarized in Table 1.

The starting model for the refinement of the 5HMF-Hb complex structure was the FUF-Hb structure—after deletion of FUF, water molecules and sulfate anions. A round of rigid body, conjugate gradient minimization and simulated annealing refinements also showed two 5HMF bound at the two symmetry-related N-terminal αVal1 nitrogens. In contrast to the FUF-Hb structure, $O_2$ molecules were ligated to the Fe atoms. Several alternate rounds of conjugate gradient minimization, simulated annealing, individual B factor refinements, and the addition of 7 sulfate anions and 538 water molecules, with intermittent manual model corrections, brought the final Rfactor to 18.3% and Rfree to 22.3% at 1.85 Å resolution. The crystallographic data for the 5HMF-Hb structure is summarized in Table 1. The atomic coordinates and structure factors have been deposited in the RCSB Protein Data Bank with accession codes 1QXD and 1QXE for the FUF- and 5HMF-Hb structures, respectively.

Structure Determinations and Refinements of the T state Complex Structures. The starting model for the refinement of the T state 5HMF-Hb structure was the isomorphous $\alpha1\beta1-\alpha2\beta2$ T state native structure (PDB code 2HHB). After rigid body refinement, and subsequent gradient minimization and simulated annealing, the electron density maps for the structure, unlike those of the R2 state complex structures, revealed only weak and undefined densities at the N-terminal αVal1 binding sites. Repeated cycles of refinements, addition of water molecules, and model building did not show improved density at the binding site to successfully model 5HMF. There were no other apparent binding sites. The final Rfactor and Rfree for the 5HMF-Hb structures are 16.3 and 20.7% at 1.86 Å resolution. Other statistics for the crystal are reported in Table 1.

TABLE 1

Crystal Information, Data Collection and Refinement Parameters for the Hb Complex Structures

|  | FUF (R2 state) | 5HMF (R2 state) | 5HMF (T state) | FUF (R state) |
|---|---|---|---|---|
| Data collection | | | | |
| Space Group | P3$_2$21 | P3$_2$21 | P2$_1$ | P4$_1$2$_1$2 |
| Cell Dimensions (Å) | 91.40 | 91.86 | 62.61 | 53.46 |
|  | 91.40 | 91.86 | 82.47 | 53.46 |
|  | 142.00 | 143.53 | 53.46 | 192.88 |
|  |  |  | 99.52 |  |
| Mol/asymmetric unit | 1 tetramer | 1 tetramer | 1 tetramer | 1 dimer |
| Resolution (Å) | 69.1–2.25 | 69.6–1.85 | 82.5–1.86 | 84.0–2.0 |
| No. of measured refl. | 124853 | 286747 | 108495 | 105005 |
| Unique reflections | 32647 | 56802 | 41917 | 18357 |
| I/sigma I | 7.0 | 12.5 | 15.8 | 13.2 |
| Compl. (%) | 97.0 | 93.1 | 90.7 | 92.0 |
| Rmerge (%)[a] | 7.5 | 6.9 | 6.5 | 6.9 |
| Refinement | | | | |
| Resolution (Å) | 69.1–2.25 | 69.6–1.85 | 52.7–1.86 | 51.5–2.0 |
| Sigma cutoff (F) | 0.0 | 0.0 | 0.0 | 0.0 |
| No. of refl. | 32645 | 56780 | 41895 | 18316 |
| Rfactor (%) | 21.7 | 18.4 | 16.3 | 21.3 |
| Rfree (%)[b] | 27.4 | 22.3 | 20.7 | 26.3 |
| Rmsd standard Geom. | | | | |
| Bond-lengths (Å) | 0.011 | 0.013 | 0.015 | 0.012 |
| Bond-angles (°) | 1.87 | 1.89 | 1.72 | 1.90 |
| Dihedral angles | | | | |
| Most favored regions | 91.4 | 92.8 | 93.6 | 92.8 |
| Additional regions | 8.6 | 7.2 | 6.4 | 7.2 |

[a]Rmerge = $\Sigma(<I> - I)/\Sigma I$.
[b]5% of the reflection which were used for the calculation of Rfree were excluded from the refinement.

The 5HMF-Hb structure, without water and ligands was used as a starting model for the refinement of the FUF-Hb structure. Similar to the 5HMF-Hb structure, refinements of the FUF-Hb structure did not result in any interpretable density at the binding pocket. The structure was not refined to completion, and detailed statistics for the crystal is not reported in the Table 1.

Structure Determinations and Refinements of the R state Complex Structures. The isomorphous α1β1 dimer R state structure (1LJW) after deletion of water molecules and phosphate anions was used as the starting model to refine the FUF-Hb structure. Similar to the T state complexes, repeated refinements of the FUF-Hb structure with model building showed only weak and uninterpretable density at the N-terminal αVal1 binding pocket. The final Rfactor and Rfree are 21.3 and 26.3 at 2.0 Å resolution, and detailed statistics for the crystal are reported in Table 1.

The FUF-Hb structure, without water and ligands was used as a starting model for the refinement of the 5HMF-Hb structure. Similar to that of the FUF crystal, refinements also showed uninterpretable density at the binding pocket, and the refinement was aborted. No detailed statistics for the crystal are reported in the Table 1.

Results

Vanillin has been clinically tested for SCD therapy, and was studied with the examined heterocyclic aldehydes, also referred to as furanic compounds. We have also previously published detailed functional and antisickling properties of vanillin (Abraham, et al., 1991). Additionally, relatively high concentrations of compounds (5–10 mM) were used to ensure complete reaction with Hb in the current studies. This is necessary, as the concentration of Hb within RBCs is approximately 5 mmol/L, and at 25% hematocrit with a blood volume of 4 L, 10 mmol/L compound is needed to produce a 2:1 compound:Hb adduct. There are two identical binding sites in Hb since it possesses a two-fold axis of symmetry.

Oxygen Equilibrium Studies with Normal Whole Blood. Table 2 summarizes the effects of four furanic compounds and vanillin (at 5 mM concentrations) on AA cell. Allosteric effectors that increase Hb oxygen affinity decrease the P$_{50}$ (left-shift the OEC)—relative to the control. This results in a negative ΔP$_{50}$ value. The most potent compound is 5HMF (ΔP$_{50}$=−17.52 mmHg), followed by 5MF (ΔP$_{50}$=−16.16 mmHg), 5EF (ΔP$_{50}$=−15.71 mmHg), and FUF (−11.35 mmHg). The poorest left shifting compound is vanillin (−6.78 mmHg). Table 2 also shows that 5HMF left-shifts the OEC in a dose-dependent manner. The Hill coefficients of the modified Hbs, with the exception of that of FUF are smaller compared to that of AA cells alone.

TABLE 2

Oxygen Equilibrium Studies with Normal Whole Blood[a]

| Compound[b] | P$_{50}$ (mmHg)[c] | ΔP$_{50}$ (mmHg)[d] | n$_{50}$[e] |
|---|---|---|---|
| Control | 25.84 ± 0.01 | — | 2.27 ± 0.20 |
| 5 mM Vanillin[e] | 19.06 ± 1.98 | −6.78 | 1.98 ± 0.23 |
| 5 mM FUF | 14.49 ± 0.06 | −11.35 | 2.30 ± 0.01 |
| 5 mM 5MF | 9.68 ± 0.24 | −16.16 | 1.70 ± 0.06 |
| 5 mM 5EF | 10.13 ± 0.75 | −15.71 | 1.77 ± 0.14 |
| 1 mM 5HMF | 19.19 ± 1.51 | −6.65 | 2.08 ± 0.14 |

TABLE 2-continued

Oxygen Equilibrium Studies with Normal Whole Blood[a]

| Compound[b] | $P_{50}$ (mmHg)[c] | $\Delta P_{50}$ (mmHg)[d] | $n_{50}$[e] |
|---|---|---|---|
| 2 mM 5HMF | 15.04 ± 0.51 | −10.80 | 1.98 ± 0.08 |
| 5 mM 5HMF | 8.32 ± 0.40 | −17.52 | 1.88 ± 0.06 |

[a]The results are the means ± S. E. for 2 measurements.
[b]The ratio of compound to Hb at 1 mM, 2 mM and 5 mM compound concentrations are 0.8, 1.6 and 4, respectively.
[c]$P_{50}$ is the oxygen pressure at which AA cells (40% hematocrit) in the absence or presence of compound is 50% saturated with oxygen.
[d]$\Delta P_{50}$ is $P_{50}$ of compound treated AA cells-$P_{50}$ of control.
[e]$n_{50}$ is the Hill coefficient at 50% saturation with oxygen.

Figure 3:
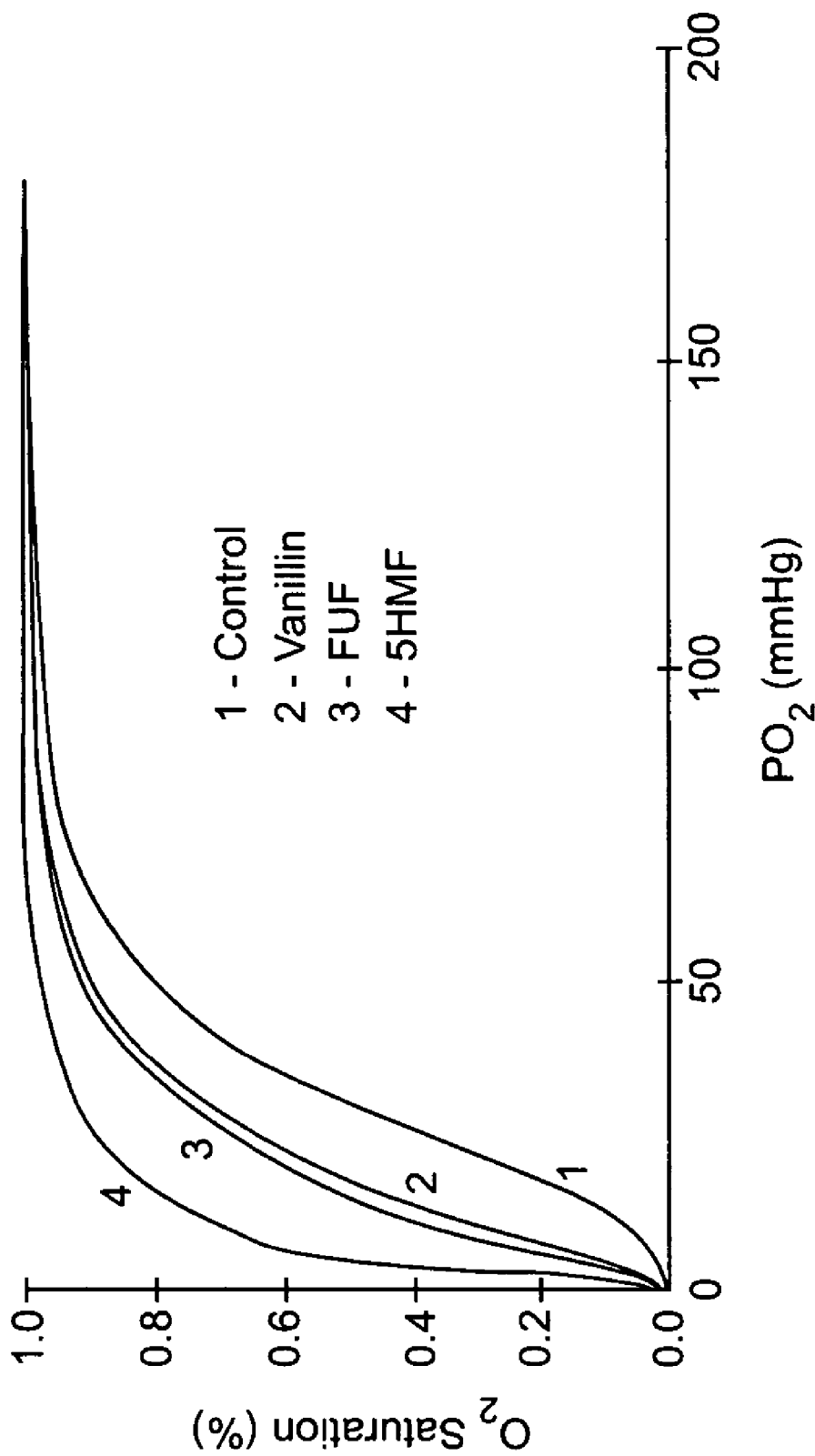
FIG. 3. Oxygen equilibrium curves of suspensions of SS cells in the absence (1) and presence of 5 mM vanillin (2), FUF (3) and 5HMF (4). Note the significant left shift caused by addition of 5HMF.

Oxygen Equilibrium Studies with Homozygous Sickle Red Blood Cells. Table 3 (columns 2 and 3) summarizes changes in $P_{50}$ and $\Delta P_{50}$ for SS cells treated with vanillin, FUF, and 5HMF at 5 mM concentration. All compounds shift the OEC to the left, and as observed in the oxygen equilibrium studies with AA cells, 5HMF is allosterically the most potent compound ($\Delta P_{50}$=−25.2 mmHg) followed by FUF ($\Delta P_{50}$=−15.8 mmHg), and lastly vanillin ($\Delta P_{50}$=−13.5 mmHg). FIG. 3 shows the OEC curve for all three compounds at 5 mM concentration, and shows that 5HMF is significantly left-shifted compared with the OEC of both FUF and vanillin. As previously observed for vanillin with both AA and SS cells (Abraham, et al., 1991), higher concentrations of tested compounds resulted in a more hyperbolic OEC from the normal sigmoidal shaped curve.

TABLE 3

Oxygen Equilibrium and Adduct Formation Studies with Homozygous Sickle Red Blood Cells[a]

| Compound | SS cells $P_{50}$ (mmHg)[b] | SS cells $\Delta P_{50}$ (mmHg)[c] | Hemolysate $P_{50}$ (mmHg) | Hemolysate $\Delta P_{50}$ (mmHg)[d] | HbS adduct (%)[e] |
|---|---|---|---|---|---|
| Control | 31.2 ± 1.0 | — | 11.2 ± 0.2 | — | — |
| Vanillin | 17.7 ± 2.2 | −13.5 | 8.1 ± 1.1 | −3.1 | 15 ± 3.6 |
| FUF | 15.4 ± 1.7 | −15.8 | 5.3 ± 0.6 | −5.9 | 24 ± 5.7 |
| 5HMF | 6.0 ± 1.2 | −25.2 | 1.8 ± 0.3 | −9.4 | 70 ± 10.0 |

[a]The results are the means ± S. E. for 2 measurements.
[b]$P_{50}$ is the oxygen pressure at which SS cells (10% hematocrit) or hemolysate (in the absence or presence of compound solubilized in DMSO) is 50% saturated with oxygen.
[c]$\Delta P_{50}$ is $P_{50}$ of compound treated SS cells or hemolysate-$P_{50}$ of control.
[d]$P_{50}$ values obtained from hemolysate after incubation of compounds with SS cells.
[e]HbS adduct values obtained from HPLC elution patterns of hemolysate after incubation of compounds with SS cells.

Figure 4A:
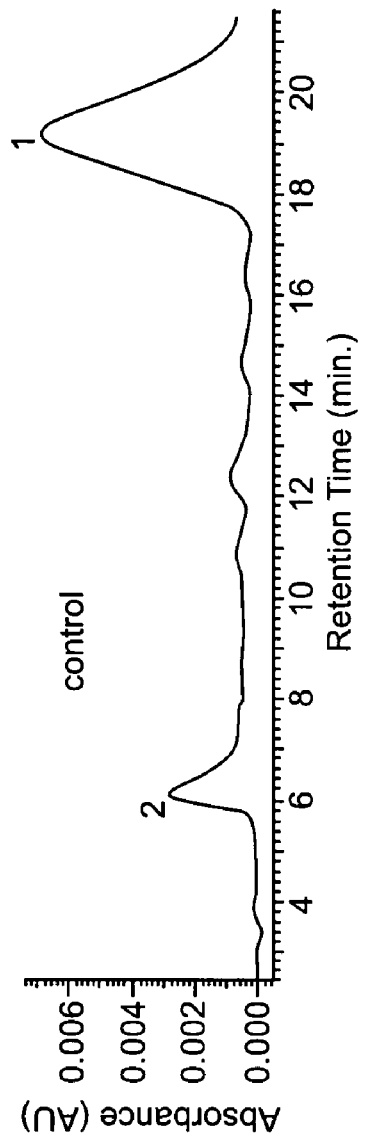
FIG. 4. Cation-exchange HPLC studies of the hemolysate from the 5HMF-reacted SS cells. Peak 1 is normal HbS, while peak 3 is the modified HbS. Peak 2 represents HbS1, a minor component that separates and elutes earlier from the major HbS peak.
Figure 4B:
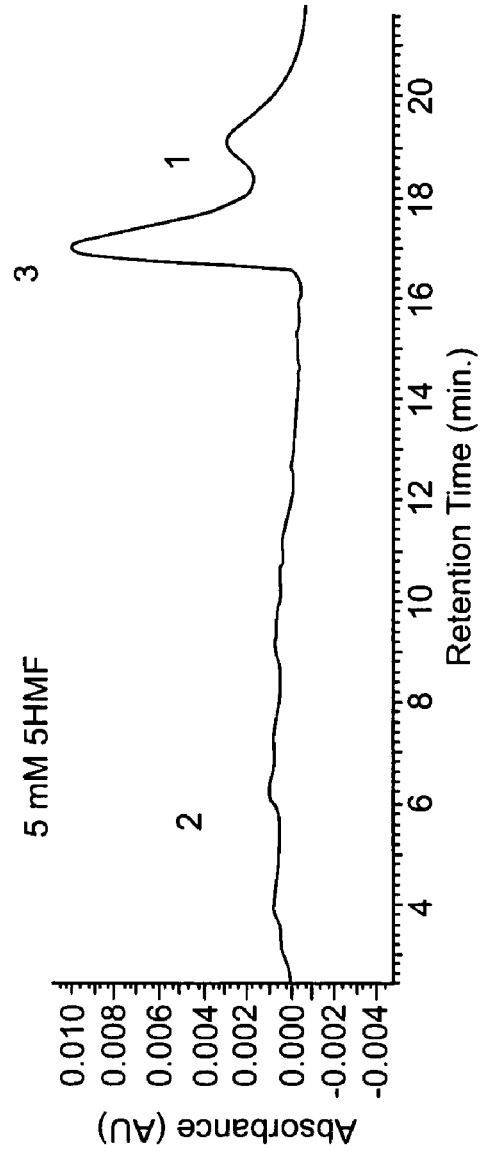

Transport through Homozygous Sickle Red Blood Cell Membrane and Reaction with HbS. These experiments were undertaken to determine if the left-shift observed for compound-treated SS cells is the result of a direct interaction of the compound with HbS, and also to determine if $P_{50}$ changes observed in SS cells treated with test compounds is attributed to the formation of different levels of compound-HbS adduct. The results are summarized in Table 3 (columns 4–6). Each of the tested compounds produces a new HbS modified peak that eluted before that of the parent HbS peak, indicating the formation of covalently modified HbS adducts. 5HMF modified HbS by the greatest degree (70%), followed by FUF (24%), and lastly vanillin (15%). FIG. 4 shows the Cation-exchange HPLC studies of the hemolysate from the 5HMF-reacted SS cells at 5 mM concentration. The compounds also shifted the OEC of the hemolysate to the left. These shifts follow the same trend observed during the normal whole blood studies. 5HMF causes the largest Hb left shift ($\Delta P_{50}$ of −9.4 mmHg), followed by FUF ($\Delta P_{50}$=−5.9 mmHg) and lastly vanillin ($\Delta P_{50}$=−3.1 mmHg).

Antisickling Studies of Compounds with Homozygous Sickle Red Blood Cells. Upon exposure of SS cell suspensions to only 4% oxygen, in the absence of test compounds, all cells underwent sickling. In the presence of vanillin, FUF, and 5HMF (at 5 mM concentrations) the percentage of SS cells decreases by 20, 30, and 90%, respectively (Table 4, columns 2 and 3). 5HMF inhibited sickling the most, followed by FUF, and vanillin. These results follow the same trend observed in the left shift of the OEC, as well as the compound-HbS adduct formation. Table 4 also shows the results of the dose-dependent antisickling effect of FUF and 5HMF. Different concentrations of these compounds decreased the formation of SS cells in a dose-dependent manner. However, unlike 5HMF, FUF did not inhibit cell sickling at lower compound concentrations (1 and 2 mM).

TABLE 4

Antisickling Studies with Homozygous Sickle Red Blood Cells[a,b]

| Compound | Sickling of SS cells (%) | Inhibition of sickling of SS cells (%) | MCV[c] (fl) |
|---|---|---|---|
| Control | 100 | 0 | 61.5 |
| 5 mM Vanillin | 80 | 20 ± 6.5 | 61.0 |
| 1 mM FUF | 100 | 0 | 60.3 |
| 2 mM FUF | 100 | 0 | 60.0 |
| 5 mM FUF | 70 | 30 ± 7.0 | 62.8 |
| 1 mM 5HMF | 87 | 13 | 62.5 |
| 2 mM 5HMF | 58 | 42 ± 1.0 | 61.0 |
| 5 mM 5HMF | 10 | 90 ± 5.0 | 61.4 |

[a]The results are the means ± S. E. for 2 measurements.
[b]Antisickling studies with SS cells (10% hematocrit) under 4% oxygen.
[c]MCV is the mean corpuscular volume.

The Effect of Compounds on Homozygous Red Sickle Blood Cell Size—As shown in Table 4 (column 4) incubation of SS cells with 1, 2, and 5 mM of FUF or 5HMF did not result in changes in cell volumes.

Crystallization Studies. Deoxygenated Hb complexed with either FUF or 5HMF crystallized in both T and R2 state conformations. The T state co-crystallized with FUF and 5HMF show only weak binding of these compounds, while the R2 state co-crystallized with these compounds show very strong binding. With compound to Hb ratios of 4:1, we observed both T and R2 state crystals in the same crystallization tubes. Interestingly, for 5HMF, more R2 state than T state crystals were always observed; for FUF the opposite was generally true. However, if a large excess of compound is used ($\geq$10 molar excess), nearly all of the co-crystallization experiments with FUF and 5HMF result in only R2 state crystals. These results suggest that 5HMF is allosterically more potent than FUF, which is consistent with the biological results.

R2 state native crystals have previously been crystallized under low salt conditions (Silva, et al., 1992), but not in high salt conditions. The ensuing structures of the R2 state co-crystals, as already pointed out, have water or $O_2$ molecules (FUF- and 5HMF-Hb complexes, respectively) coordinated to the Fe atoms. In reality, it is hypothesized that the ligands are actually a mixture of $O_2$, CO, and water, as analysis of the R2 state complexes showed the presence of COHb, metHb, and oxyHb (60–85%), versus approximately 16% for the T state co-crystals. The presence of the ligands in the R2 state co-crystals could be due to the fact that the anaerobic chamber used in these experiments may not have been completely devoid of oxygen during the crystallization setup. Interestingly, the T state co-crystals that occurred in the same solutions as the R2 state co-crystals did not show any residual density for ligand binding to Fe. These observations underscore the high-affinity nature of relaxed state Hb compared to tense state Hb. These results also clearly show that the R2 quaternary structure is physiologically important as previously pointed out (Srinivasan & Rose, 1994).

Unlike the T and R2 crystallization results, and quite significantly, repeated R state crystallization experiments did not result in any co-crystals, especially at high compound concentrations ($\geq 5$ molar excess to the Hb tetramer). However, if low compound concentrations (4 molar excess to the Hb tetramer) were used, very few R state co-crystals for both FUF and 5HMF were observed, with most of the complex remaining in solution. We should point out that, we were able to easily obtain R state native crystals (control experiment without adding any compound) under these same crystallization conditions.

Descriptions of the R2 State Complex Structures. Both FUF-Hb and 5HMF-Hb complex structures contain one $\alpha 1\beta 1-\alpha 2\beta 2$ tetramer in the asymmetric unit. The R2 state complexes and R2 state native have essentially the same Hb quaternary structures (rmsds of ~0.4 Å). However, comparison of the R2 state complex structures with R (PDB code 1AJ9) and T (PDB code 2HHB) native Hb structures show very significant quaternary structural differences, with rmsd of ~1.8 Å and ~3.3 Å, respectively. As previously analyzed and reported by Silva et al., (1992) for R, T and R2 native Hb structures, the allosteric transitions between the R2 complex structures and those of the R and T structures show extensive reorganization of the $\alpha 1\beta 2\alpha 1\alpha 2$ and $\beta 1\beta 2$ interfaces in the three Hb states. The structures were superimposed using the invariant $\alpha 1\beta 1$ dimer (C$\alpha$ residues) on the BGH frame as defined by Baldwin & Chothia (1979).

Following are detailed descriptions of the interactions between R2 state Hb, and the two compounds, FUF and 5HMF. Both furanic compounds are well ordered with occupancies of approximately 100%. The compounds bind in a symmetry-related fashion at the $\alpha$-cleft to the two N-terminal $\alpha$Val1, with the aldehyde functional group forming a covalent bond with the free nitrogen of the valine. Specific interactions between the compounds and the protein will be discussed for only the $\alpha 1$Val1 binding site, as the other symmetry-related molecule engages in similar, but opposite interactions at the $\alpha 2$Val1 binding site. A covalent interaction between the aldehyde and $\alpha 1$Val1 nitrogen directs the furan ring of the compounds toward the central water cavity. In the FUF-Hb structure, the bound compound appears to have two alternate conformations that differ by almost 180°. The aromatic oxygen engages in a very weak intersubunit hydrogen bond with $\alpha 2$Ser138 OG (3.6 Å), which serves to tie the two $\alpha$-subunits together. Interestingly, if the compound is rotated to its alternate conformation, the oxygen faces the water cavity and engages in a weak intrasubunit hydrogen bond with $\alpha 1$Ser131 OG (3.5 Å). There are very few hydrophobic interactions (<3.8 Å) between the furan ring and the residues Lys127 and Ala130.

Unlike FUF, there is no evidence of compound rotation of the bound 5HMF molecule, and it assumes a conformation with the ring oxygen facing the water cavity. The observed interaction between FUF and $\alpha$Ser138 OG is therefore absent in the 5HMF-Hb complex structure. Similar to FUF, the ring oxygen of 5HMF engages in a stronger intrasubunit hydrogen bond with $\alpha 1$Ser131 OG (3.1 Å), compared to FUF binding. In addition, the 5-hydroxymethyl substituent of 5HMF also makes a strong intrasubunit hydrogen bonding interaction with $\alpha 1$Thr134 OG1 (2.6 Å); this interaction is absent in the FUF-Hb complex structure. While FUF ties the two $\alpha$-subunits together by making a weak intersubunit hydrogen bond with $\alpha 2$Ser138 OG, the two 5HMF molecules are joined together by a strong network of six water-mediated hydrogen bonds, through the hydroxyl and the ring oxygen moieties that tie the two $\alpha$-subunits together. Some of these water molecules are conserved in the FUF binding pocket, but they are mobile and do not engage in hydrogen bonding contact with the FUF molecules. Like the FUF-Hb structure, there are very few hydrophobic interactions (<3.8 Å) between 5HMF and Hb. The increased number of interactions between 5HMF and protein residues (versus FUF), as well as the strong water-mediated hydrogen bonds that tie the two $\alpha$-subunits together in the 5HMF complex structure, may partly explain why 5HMF is allosterically more potent than FUF.

Descriptions of the T State Complex Structures. Both FUF-Hb and 5HMF-Hb complex structures contain one $\alpha 1\beta 1-\alpha 2\beta 2$ tetramer in the asymmetric unit. Unlike the R2 complex structures, the T state complexes do not show clearly defined compound binding. Some examined co-crystals did show more compound density than others; however repeated model building to improve compound density was not successful enough to allow for reliable compound fitting. The T state complexes and T state native have essentially the same Hb quaternary structures (rmsds of ~0.4 Å). Superposition of the $\alpha$Val1 binding sites also shows very few structural differences. Further, we should point out that in our laboratory we have been able to easily isolate T state structures that have covalently bound compounds, with clearly defined electron density at the N-terminal $\alpha$Val1 using the same T state crystallization conditions as described above (Abraham, et al. 1995; Boyiri, et al., 1995).

Descriptions of the R State Complex Structures: Both FUF-Hb and 5HMF-Hb complex structures contain one $\alpha 1\beta 1$ dimer in the asymmetric unit. Surprisingly, the few R state crystals that were obtained during these experiments show only sparse density at the N-terminal $\alpha$Val1 binding sites. Even though the R complex and native quaternary structures are indistinguishable (rmsds ~0.4 Å), the C-terminus (residues Trp140 and Arg141) display significant positional differences. In the complex structures, these residues have rotated away at the $\alpha$Lys139, displacing $\alpha$Arg141 by almost 180° from its position in the native structure, while $\alpha$Tyr140 has oriented away by ~2 Å. $\alpha$Tyr140 OH now engages in hydrogen bonds with $\alpha$Val93 O and $\alpha$Pro95 N in the complex structures, versus diagnostic R state native hydrogen bonds with $\alpha$Val93 N and O. The reorientation of the C-terminus has led to a much bigger binding cleft in the R complex structures to allow binding of the compound, albeit weak. This contrasts with the native structure, where the C-terminal residues are found to be sterically blocking this binding site.

Discussion

These studies have identified furan-based derivatives, which are naturally occurring in a number of foods, as potential new therapeutics to treat SCD. Results from these studies clearly indicate that these compounds possess the ability to: (1) pass through RBC membranes; (2) react with HbS; and (3) allosterically shift the Hb OEC to the high-affinity state, which does not form HbS polymers. Furthermore, we have found that the change in the oxygen affinity of SS cell suspensions caused by these compounds depends on the degree of binding to HbS; 5HMF showed the highest amount of compound-HbS adduct, and as expected, was the most potent OEC left shifter. Also, the results clearly suggest that substitution, as well as substitution type at the 5-position of the central furan ring is important to biological activities. 5HMF, which possesses an alkyl alcohol at the 5-position of the furan ring, is more potent than either 5MF or 5EF (FIG. 2), both of which possess hydrophobic moieties at this position. FUF, without a substitution is the least potent. This is consistent with the crystallographic results, which indicate that the hydroxyl moiety of 5HMF is intimately involved in interactions that stabilize the relaxed state. The Hill coefficients of the modified Hbs are relatively smaller compared to the unmodified Hb, suggesting a decrease in cooperativity. This is expected because of the apparent weakening of interdimer interactions by the binding of the compounds to the T state, leading to increased oxygen affinity, reduced cooperativity, and a shift toward the high-affinity Hb.

Antisickling Activities of the Furanic Compounds. Results from the screening of FUF and 5HMF with SS cells show that these compounds have strong antisickling properties, stronger than other known antisickling aldehydes. At 5 mM concentration, 5HMF inhibited cell sickling approximately 4 and 2.5 times more than vanillin and FUF, respectively. Remarkably, even at 2 mM concentration, 5HMF reduces cell sickling by 42%, twice as much as vanillin at 5 mM concentration. 5HMF, which modifies HbS the most, is the most potent left-shifting compound, as well as the most potent antisickling agent; the converse is true for vanillin. Thus, the antisickling action of these compounds seems to result from their ability to bind to HbS and left shift the OEC toward the high-affinity state. And even though the antisickling activities of 5MF and 5EF (FIG. 2) have not been determined, based on structure-activity relationships, we predict that both compounds will exhibit antisickling activities that lie between those of FUF and 5HMF.

Also significant is the fact that the compounds did not dehydrate SS cells. Polymerization of HbS and the sickling of SS cells are linked to the intracellular concentration of HbS, therefore, any agent that causes dehydration of RBCs would increase the molar concentration of HbS, and presumably increase polymer formation. Furthermore, although not reported, the compounds did not promote formation of metHb or membrane-associated denatured Hb.

Mechanism for the Antisickling Activities of the Furanic Compounds. The results from these studies clearly show that the furanic compounds covalently bind to and destabilize the T state and/or stabilize the relaxed state HbS. As a result, the allosteric equilibrium left shifts toward the more soluble, high-affinity HbS in the form of R2 conformation. To our knowledge, this is the first such reported observation in the literature that shows a compound induced conformational change of a T state Hb to R2 state Hb, leading to isolation of R2 co-crystals from deoxy Hb solution. We hypothesized this to be the underlying cause for the observed antisickling activities. To understand the atomic-level mechanism driving the observed biological activities of the compounds, we refer to two landmark publications by Abraham's group (Abraham, et al., 1995; Boyiri, et al., 1995) in which the authors hypothesized that agents such as FSA (FIG. 2), that form Schiff base adducts with the N-terminal αVal1 nitrogen of the T state, and provide groups for both salt bridge and hydrogen bonding with the opposite dimer (across the two fold axis), add more constraints to the T state. These added constraints shift the allosteric equilibrium toward the low-affinity T state. In contrast, agents such as DMHB (FIG. 2) which bind to the T state in a similar fashion, but do not engage in any salt bridges/hydrogen bonding interactions with the opposite dimer, left shift the OEC. It is hypothesized that these agents disrupt a water-mediated linkage between the N-terminal αVal1 and the C-terminal αArg141 of the opposite dimer, which leads to the destabilization of the T state, and as a result the allosteric equilibrium is shifted toward the high-affinity R state. Unlike FSA, the furanic compounds lack a carboxylate substituent that would engage in intersubunit stabilizing interactions when bound to the T state. What is not clear is how these compounds bind to the T state, as the crystallographic studies show only weak and undefined compound density. However, If we assume that the compounds bind with the same orientation as observed in the R2 state complex structures, a hypothetical fit of 5HMF into the T state N-terminal αVal1 binding site (with the aid of the weak compound density) shows this compound engaging in only intrasubunit interactions with αThr134 OG1 and αSer131 OG. Thus it seems the furanic compounds bind to the N-terminal αVal1 site of the T state, disrupt the native water mediated hydrogen bond between αVal1 and αArg141, and destabilize the T-state. The result of this destabilization is an allosteric shift to the high-affinity, relaxed Hb in the form of the R2 state. This mechanism is consistent with the fact that: (1) R2 state crystals were formed from deoxy Hb/furanic compound solution and (2) T state crystallization in the absence of furanic compound did not result in R2 state crystals. In fact, all of the T state crystals that were isolated in conjunction with the R2 state crystals had only weak compound density—clearly these T state crystals did not have enough bound compound to effect the allosteric shift. Consistent with this observation is the fact that the addition of a large excess of furanic compound resulted in 100% formation of R2 state co-crystals from the deoxy Hb complex solution—due to saturation of the binding site of all the deoxy Hb molecules.

The observed functional and crystallographic results, as well as the proposed mechanism, raise an interesting issue of why R2 state crystals and not R state crystals form during the T state crystallization experiment. Visual analyses and molecular docking studies of the N-terminal αVal1 binding pockets of known T, R and R2 native Hb structures may shed light on the above question. The native structures were superimposed using the invariant α1β1 dimer (Cα residues) on the BGH frame (Baldwin & Chothia, 1979). In both the T and R2 states, the binding pockets of Hb are strikingly larger than that of the R state. Docking studies show that 5HMF can easily fit the T and R2 state binding pockets without steric interference; in contrast, the N-terminal αVal1 binding pocket of the R state native Hb is sterically crowded due to the presence of the C-terminus residues of Tyr140 and Arg141. Thus, for 5HMF to be able to bind to the R state there must be rearrangements of the binding pocket residues. This is exactly what occurs in the R state complex structures, which show larger binding pockets compared to the native structure. It seems reasonable that the penalty for rearrangement of the binding pocket residues in the R state should considerably slow the incorporation of the compound into the binding site (compared to the T and R2 states). These observations may partly explain why binding of the furanic compounds to deoxy Hb destabilized this protein to the R2 state and not to the R state. Also, we can reasonably assume that these compounds bind directly and with higher affinity to the R2 state compared to the R state, and the compound-HbS adducts observed during the HPLC analyses of SS cells are mostly due to the incorporation of the compounds into the R2 state. We should point out that there is no obvious explanation why we didn't observe R2 state crystals from the aerobic crystallization of compound-COHb solution. However, it is quite possible that the R2 state complex existed in solution but failed to crystallize out. This is consistent with the fact that almost all of the aerobic crystallization experiments did not result in crystals, and the few that did, only produced a few R state crystals, with the majority of the complexed species remaining in solution.

Based on the results, it is hypothesized that the observed differences in the biological activities of the examined furanic compounds are due to their modes of binding to both the T and R2 state. In the R2 state complex structures, 5HMF possesses the ability to stabilize the relaxed conformation to a greater degree than FUF (as discussed above). Modeling of the two compounds into the T state also indicates that 5HMF would bind more tightly to the T state than FUF. Therefore, in the absence of intersubunit salt bridge interactions by these compounds in the T state, it is expected that 5HMF would destabilize the T state more than FUF.

Studies by Abraham, et al. with vanillin (1991), Johnson et al. with pyridoxal (1985), and Park et al. with substituted isothiocyanates, (2003) have suggested that the antisickling effects of these compounds are due to the direct inhibition of T state polymer formation and/or increased formation of R state molecules. These studies surmised the formation of R state Hb from the ability of the compounds to shift the OEC to the left. Clearly, our studies unequivocally show that it is the R2 state, rather than the R state, which is formed when the OEC is shifted to the high-affinity Hb. Thus, the mode of action of the furanic compounds seems to be different from these other antisickling compounds.

Conclusions. A HbS homozygote with a blood volume of 4 L and 25% hematocrit has approximately 5 mmol of HbS. For complete modification of HbS with 5HMF (mwt=126), 10 mmol will be needed, since two molecules bind to Hb, translating into 1.26 g of compound. Since 30% modification of HbS would be enough to achieve clinical benefit, in principle, we need only administer 378 mg of this compound (assuming the drug targets HbS only). For a compound like 5HMF, which is non-toxic, a large dosage may be acceptable, as certain foods that are consumed on a daily basis, such as coffee and caramel products possess concentrations of 5HMF that sometimes exceed 6 g/kg (Janzowski, 2000). In rats, the acute oral $LD_{50}$ of 5HMF is 2.5 g/kg for males and 2.5–5.0 g/kg for females (US EPA, 1992). In comparison, vanillin, which is considered non-toxic, has an acute oral $LD_{50}$ of 1.58 g/kg. The other furanic compounds also occur in nature, and with the exception of FUF, there are no reports about possible adverse effects of MF and EF. The antisickling agents, vanillin and 12C79 also bind covalently to Hb, and both have been shown to be clinically non-toxic (Fitzharris, et al., 1985; Orringer, et al., 1988). Remarkably, 5HMF is more than four times as effective compared to vanillin, which is currently under clinical studies for treatment of SCD. Thus, the furanic compounds may also be viable drug molecules. The results from this study also present a coherent picture of the antisickling potencies and atomic-level mechanisms of new antisickling agents. With this information, it will be possible to perform structure-activity studies that will result in the development of analogs with enhanced potency.

Example 2

In Vivo Antisickling Effect of 5-HMF

In vivo antisickling effect of 5-HMF was investigated using transgenic (Tg) mice that produce human Hb S. Since the blood of wild type mice has an extremely right-shifted OEC (P50 of mouse blood: 40–44 mm Hg) as compared with the OEC of human blood (P50 of AA cells: 26.5 mm Hg; SS cells: 32 mm Hg), Tg sickle mice that produce approximately equal amounts of human and mouse β-globin and 100% human $β^s$-globin were used in this study. The P50 of these mice are between 26 and 34 mm Hg depending on the percentage of mouse β-globin. We used 5% oxygen (5% $O_2$, 95% $N_2$), because they develop pulmonary sequestration almost exclusively upon exposure of these mice to 5% $O_2$. Although similar changes occurs under oxygen pressures between 6 and 10 mm Hg, not all mice develop hypoxia-induced pulmonary sequestration indicating that high numbers of Tg sickle mice are necessary to obtain statistically significant results. Upon exposure to hypoxia, we determine the percentage of sickled cells in the blood as well as the survival time. 5HMF (100 mg/kg body weight) dissolved in a small volume of DMSO was diluted with saline before i.p. injection. In the hypoxia experiments, the Tg sickle mice were exposed to hypoxia for up to 1 hr; any surviving mice at 1 hr were euthanized by cervical dislocation under anesthesia. In all cases, after the mouse died, it was immediately dissected. The heart, lungs, brain, liver, spleen, and kidneys were fixed in 10% phosphate-buffered formalin. Tissue samples were embedded in paraffin according to standard methods. Sections were cut and stained by a hematoxylin-eosin solution for light microscopy.

Results

Figure 5:
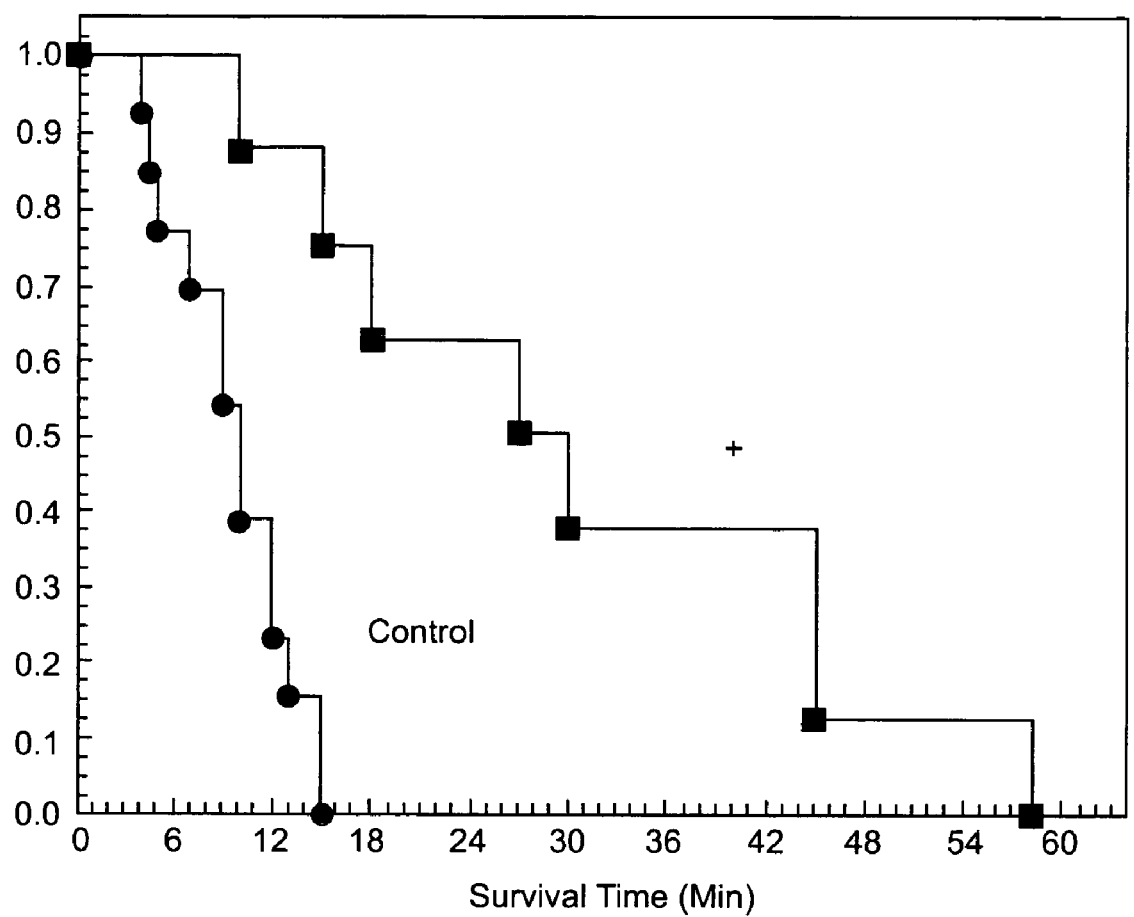
FIG. 5. Kaplan-Meier Survival plot of control and 5HMF (AMS-13)-treated Tg sickle mice.
Figure 6:
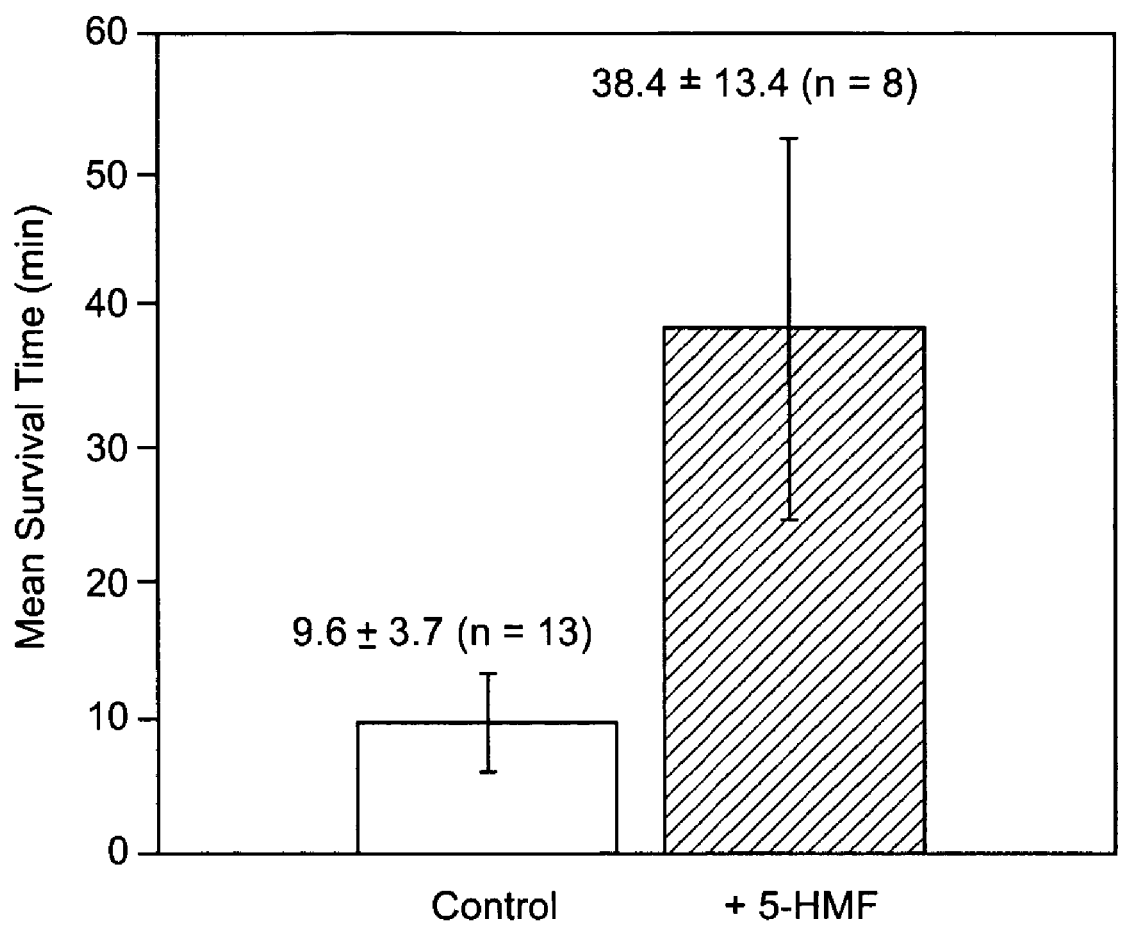
FIG. 6. Mean survival time of control and 5HMF (AMS-13)-treated Tg sickle mice.
Figure 7:
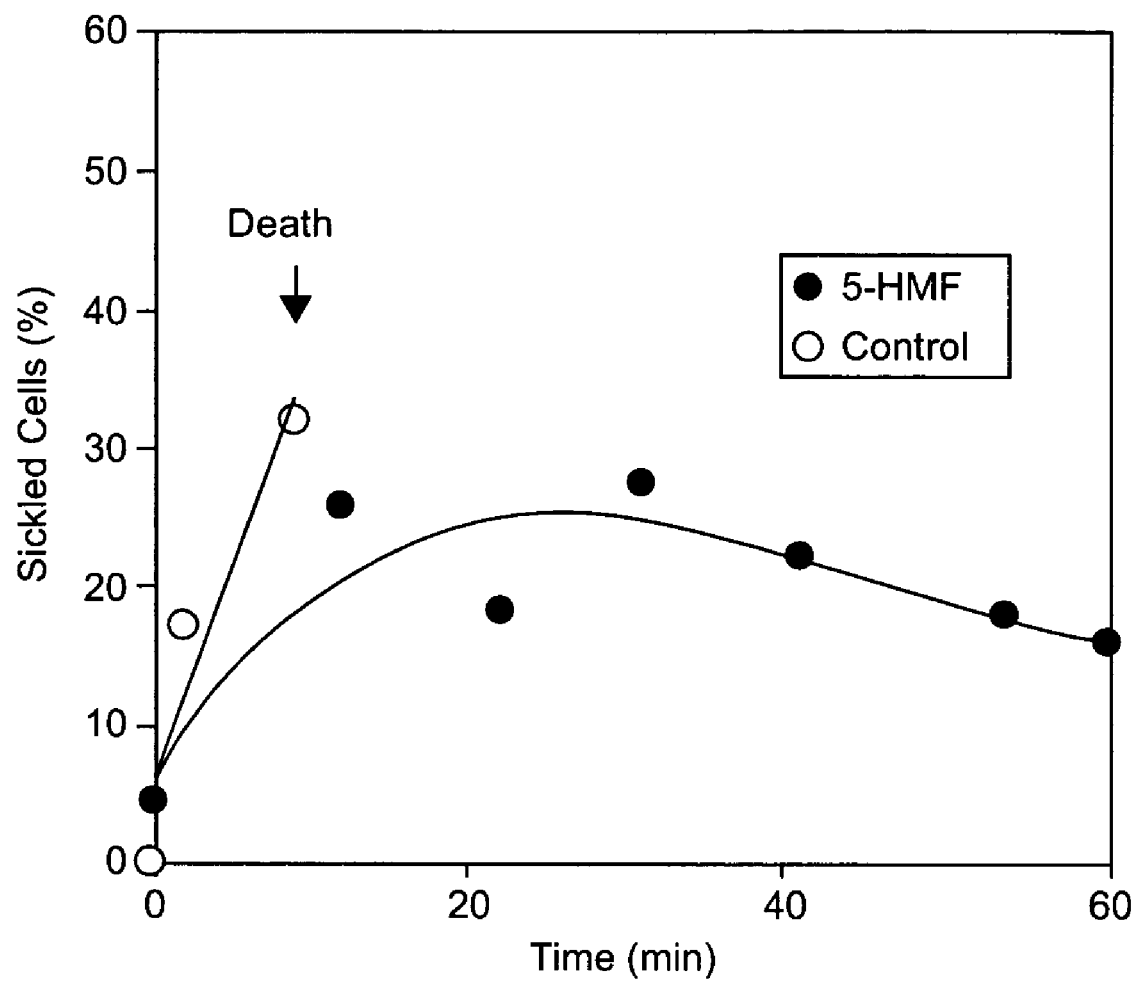
FIG. 7. The effect of 5HMF (AMS-13) on the percentage of sickled cells in the arterial blood of Tg sickle mice that were exposed to severe hypoxia (5% oxygen). Without treatment (Control), the percentage of sickled cells increased sharply and the animal died within 15 min. Pretreatment of the mice with 5HMF prolonged the survival time significantly. The drug also reduced the percentage of sickled cells.

FIG. 5 shows the Kaplan-Meir survival plot for control and Tg sickle mice pretreated with 5HMF. Without treatment, Tg sickle mice exposed to 5% oxygen die within 15 min due to pulmonary sequestration. Upon pretreatment of Tg sickle mice with 5HMF, more than half of the mice survived for longer than 25 min. As shown in FIG. 6, the mean survival time of control mice was 9.6 3.7 (N=13), while the mean survival time of mice pretreated with 5HMF was 38.4 mm Hg (n=8). Morphology of SS cells in the arterial blood at times 0, 10, 20, 30, 40, 55 and 60 min were investigated. The time course of the percentage of sickled cells in the tail artery of control and 5HMF-treated mice is shown in FIG. 7. Changes in the percentage of sickled cells in the arterial blood of one of the Tg sickle mice that were exposed to hypoxia (5% oxygen) were investigated. The percentage of an untreated mouse increased from almost zero percentage to over 30% and the animal died in 15 min. Histopathological studies showed that capillaries and small blood vessels in the lungs of these mice were packed by sickled cells. The percentage of sickled cells in one of the mice treated with 5HMF (100 mg/kg body weight) showed that although the percentage of sickled cells increased, the sickled cells are so called partially oxygenated sickled cells (POSCs) with blunt edges (Asakura, 1994). These cells are flexible and can pass through capillaries. Upon conversion of POSCs to partially deoxygenated sickled cells (PDSCs), they are rigid and trapped in the encountered capillaries. 5HMF not only reduced the formation of POSCs, but also prevented the conversion of flexible POSCs to rigid PDSCs.

CONCLUSION

Thus in vivo experiments using transgenic sickle mice that produce human sickle Hb showed that pretreatment of the mice with 5HMF (intraperitoneal administration) significantly prolonged the survival time under severe hypoxic conditions (5% oxygen). These results indicate that 5HMF is a new antisickling agent that can passes through red blood cell membrane, forms Hb adduct and inhibit hypoxia-induced sickling of SS cells.

Example 3

Generic Synthetic Schemes for Making Representative Compounds of the Invention (ref. Vogel's Textbook of Practical Organic Chemistry, 5$^{th}$ edition, 1978, by Brian S. Furniss et al.)

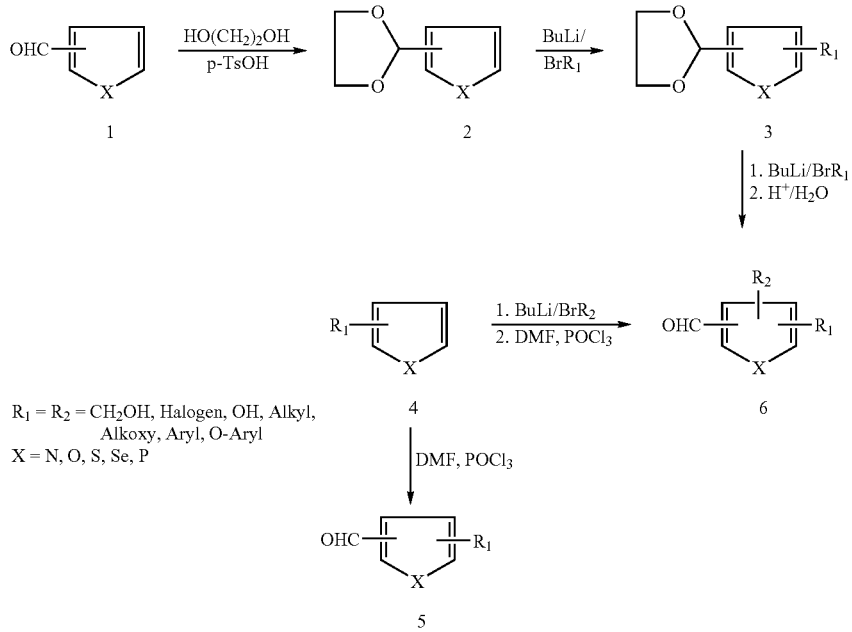

$R_1 = R_2 = CH_2OH$, Halogen, OH, Alkyl, Alkoxy, Aryl, O-Aryl
$X = N, O, S, Se, P$ The preparation of the monosubstituted aldehydes 5 involved the use of the classical Vilsmeier reaction (dimethylformamide/phosphorous oxychloride) with the appropriate substituted starting material.

The preparation of the disubstituted aldehydes, 6 can be accomplished in two ways. Starting with the appropriate monosubstituded compound 4, will be lithiated at 78° C. with butyl lithium and quenched with the appropriate bromoalkyl followed by the Vilsmeier reaction to yield the required aldehyde 6. Alternatively, starting with the protected aldehyde 2, compound 6 will be prepared by lithiation with the appropriate bromoalkyl compounds at 78° C. followed by acidic hydrolysis to yield the required aldehyde. 6.

Example 4

Prodrug Forms of 5-Membered Heterocyclic Antisickling Agents to Treat Sickle Cell Disease A. A generic synthetic scheme for making representative prodrug compounds in Formulas 6 and 11 is given in Scheme 2 below.

SCHEME 2

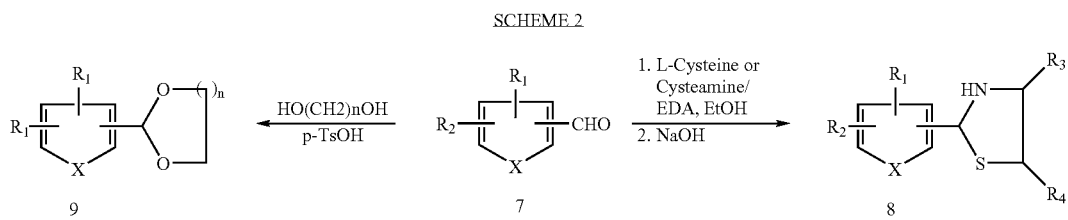

$R_1$, $R_2$ are optional and if present are independently
H, OH, Halogen, $CH_2OH$, Alkyl, Alkoxy, Aryl, O-Aryl
X = NH, O, S, Se, P
n = 0–4

L-Cysteine, $R_4$ = H,
$R_3$ = $CO_2Et$ or $CO_2H$
Cysteamine, $R_3$ = $R_4$ = H General Preparation of 5-membered Heterocyclic Thiazolidine, 8

(Huang, T-C; Huang, L-Z; Ho, C-T, J. (1988), *Agric. Food Chem.* 46, 224)

To a solution of appropriate substituted L-cysteine ethyl ester hydrochloride or cysteamine and ethyl-diisopropyl amine in anhydrous ethanol at room temperature will be added 5-hydroxymethyl-furan-2-carbaldehyde in anhydrous ethanol. The reaction mixture will be stirred at the same temperature over night. The mixture will be diluted with water and the product extracted with ethyl acetate. The organic phase will be dried, evaporated, and the product purified by flash chromatography on silica gel to yield the derivative of the thiazolidine compound 8. Where applicable in the case of L-cysteine ester analog, the ester substitutent will be hydrolyzed to the corresponding acid derivative by alkaline hydrolysis using sodium hydroxide.

General Preparation of 5-membered Heterocyclic Dioxolane, 9

(Abraham, D. J., Safo, M. K., Boyiri, T., Danso Danquah, R., Kister, J., and Poyart, C. (1995), *Biochemistry* 34, 15006–15020)

A solution of the appropriate 5-membered heterocyclic aldehyde 7, alkyl glycol and catalytic amount of p-toluenesulfonic acid monohydrate will be stirred at reflux temperature with Dean Stark apparatus for about 12 hours. The reaction mixture will be cooled, washed with aqueous sodium bicarbonate, dried and the solvent evaporated. The product will be purified by flash chromatography on silica gel to yield the derivative of the dioxolane, 9.

B. Synthesis of 5-hydroxymethyl-2-furfural-thiazolidine-4-carboxylic acid ethyl ester (MSDD1), a Prodrug of 5-HMF A prodrug form of 5HMF, 5-hydroxymethyl-2-furfural-thiazolidine-4-carboxylic acid ethyl ester (MSDD1) was synthesized. MSDD1 has the active aldehyde moiety protected from being easily metabolized in the intestines into the inactive acid derivative. This protection leads to increase bioavailability and half-life of 5HMF in vivo. For the synthesis, a stirring solution of 5HMF (1.51 g, 12 mmol) in absolute ethanol (30 mL) was added a solution of L-cysteine ethyl ester hydrochloride (2.23 g, 12 mmol) and N-ethyldiisopropylamine (2.55 g, 12 mmol) in absolute ethanol (30 mL) The reaction mixture stirred at room temperature overnight. The mixture was diluted with water (100 mL) and the product extracted with ethyl acetate (3×50 mL). The organic phase was dried, evaporated and the product was purified by flash chromatography on silica gel to give 2.77 g of product.

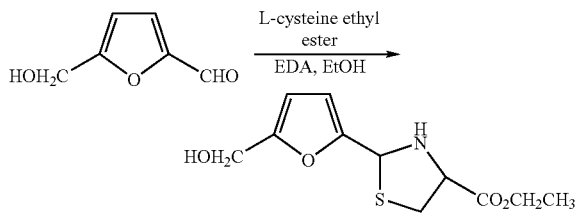

C. Oxygen Equilibrium Curve Studies of MSDD1 in Normal Whole Blood:

MSDD1 was tested in normal adult whole blood under in vitro conditions to find out whether 5HMF with its active aldehyde protected by the L-cysteine ethyl ester would have an effect on the OEC of whole blood using multi-point tonometry. The test was conducted as described for 5HMF under Example 1, subheading "*Oxygen Equilibrium Studies with Normal Whole Blood*". The whole blood oxygen equilibrium studies demonstrate that while 5HMF (with its free active aldehyde unprotected) is able to shift the OEC to the left, the prodrug of 5HMF, (with the aldehyde protected) clearly does not have effect on the OEC. This suggests that the aldehyde, which is the active functional group, is still protected by the thiazolidine-4-ester group and did not hydrolyze during the in vitro test. This is expected since the conditions at which the in vitro studies were conducted were not expected to lead to the hydrolysis of the thiazolidine-4-ester group to free the active 5HMF compound.

Example 5

Methods for Increasing Tissue Hypoxia for Treatment of Cancer

The compounds or the present invention are also useful in the treatment of cancer. The 5-membered heterocylic aldehydic compounds and their protected aldehydic derivatives bind to and destabilize the tense (T) state hemoglobin, resulting in the switch of the allosteric equilibrium in favor of the high-affinity Hb in the form of R2-state Hb. Binding to Hb, shifts the oxygen equilibrium curve to the high-affinity R2-state hemoglobin. The compounds thus induce normal tissue and tumor hypoxia by binding to hemoglobin, increasing its affinity for oxygen and thereby reducing oxygen availability to tissues. Therefore these compounds are of interest as possible potentiators of bioreductive agents and/or hyperthermia in cancer treatment.

The reduction of oxygen available to tissues also leads to protection against radiation damage during X-ray radiation therapy.

The invention includes 5-membered heterocyclic aldehydic and protected derivatives, that are more potent than 12C79 in stabilizing the high-affinity Hb. Additionally, the basis of the allosterism of these compounds is understood on molecular level, making it easier to design more potent effectors. Thus, these compounds improve on known aldehydic hypoxic agents by their potency and efficacy.

Example 6

In Vitro Oxygen Equilibrium Studies of Thiophene Analogs of the 5-Membered Heterocyclic Anti-sickling Agents with Normal Whole Blood The following compounds: 5-Bromo-2-thiophenecarboxyaldehyde, 4-Bromo-2-thiophenecarboxyaldehyde and 3-Methyl-2-thiophenecarboxyaldehyde were purchased from Aldrich Chemical Company. Normal blood samples (hematocrit 40%) in the presence of 5 mM 5-Bromo-2-thiophenecarboxyaldehyde, 4-Bromo-2-thiophenecarboxyaldehyde and 3-Methyl-2-thiophenecarboxyaldehyde (solubilized in DMSO) were equilibrated at 37° C. for 1 hr. The samples were then incubated in IL 237 tonometers (Instrumentation Laboratories, Inc. Lexington, Mass.) for approximately 10 min at 37° C., and allowed to equilibrate at oxygen tensions 7, 20, and 60 mmHg. The samples were aspirated into an IL 1420 Automated Blood Gas Analyzer and an IL 482 or IL 682 Co-oximeter (Instrumentation Laboratories) to determine the pH, $pCO_2$, $PO_2$ and the Hb oxygen saturation values ($sO_2$). The $PO_2$ and $sO_2$ values at each oxygen saturation level were then subjected to a non-linear regression analysis using the program Scientist (Micromath, Salt Lake City, Utah) to calculate the $P_{50}$ and Hill coefficient values ($n_{50}$). $P_{50}$ is the oxygen pressure in mmHg at which Hb is 50% saturated with oxygen.

Results: As shown in Table 5, all three thiophene compounds shift the OEC curve to the left, similar to the above studied furanic compounds. The studies also indicate that the thiophene compounds (like the furanic compounds) possess the ability to: (1) pass through RBC membranes; (2) react with HbS; and (3) allosterically shift the Hb OEC to the high-affinity state, which does not form HbS polymers. Also, the results suggest that substitution, as well as substitution type on the central thiophene ring is important to biological activities. This studies show that the thiophene analogs are also potential anti-sickling agents.

TABLE 5

Results of in Vitro Whole Blood Studies with Thiophene Aldehydic Compounds

| Compound | $P_{50}c$ | $P_{50}d$ | $\Delta P_{50}$ | $n_{50}$ |
|---|---|---|---|---|
| 5-Bromo-2-thiophenecarboxyaldehyde | 27.73 | 21.96<br>20.24 | −6.63 | 2.35 |
| 4-Bromo-2-thiophenecarboxyaldehyde | 27.73 | 16.85<br>17.49 | −10.56 | 2.41 |
| 3-Methyl-2-thiophenecarboxyaldehyde | 28.10 | 21.55<br>20.63 | −7.01 | 2.35 |

The analyses were carried out at a final compound concentration of 5 mM. $P_{50}c$ control value in the absence of compound in mmHg. $P_{50}d$ value in the presence of compound in mmHg. $\Delta P_{50} = (P_{50}d - P_{50}c)$ in mmHg. The Hill coefficient at 50% saturation ($n_{50}$) in the presence of compound. Each measurements were repeated at least twice.

REFERENCES

1. Abraham, D. J., Mehanna, A. S., Wireko, F. C., Whitney, J., Thomas, R. P., and Orringer, E. P. (1991) Vanillin, a potential agent for the treatment of sickle cell anemia, *Blood* 77, 1334.
2. Abraham, D. J., Safo, M. K., Boyiri, T., Danso Danquah, R., Kister, J., and Poyart, C. (1995) How allosteric effectors can bind to the same protein residue and produce opposite shifts in the allosteric equilibrium, *Biochemistry* 34, 15006.
3. Adachi, K., and Asakura, T. (1980) Polymerization of deoxyhemoglobin C Harlem (β6Glu-Val, β73Asp-Asn), *J. Mol. Biol.*, 144, 467.
4. Arnone, A. (1992) X-ray diffraction study of binding of 2,3-diphosphoglycerate to human deoxyhaemoglobin, *Nature* 237, 146.
5. Asakura, T. (1979) Automated method for determination of oxygen equilibrium curves of red cell suspensions under controlled buffer conditions and its clinical applications, *Crit. Care Med.* 7, 391.
6. Asakura, T., Ohnishi, S. T., Adachi, K., Ozgul, M., Hashimoto, M., Singer, M., Russell, M. O., Schwartz, E. (1980) Effect of cetiedil on erythrocyte sickling: new type of antisickling agent that may affect erythrocyte membranes. *Proc. Natl. Acad. Sci., USA*, 77, 2955.
7. Asakura, T., and Mayberry, J. (1984) Relationship between morphologic characteristics of sickle cells and method of deoxygenation, *J. Lab Clin. Med.* 104, 987.
8. Asakura T, Mattiello J A, Obata K, Asakura K, Reilly M P, Tomassini N, Schwartz E, Ohene-Frempong K. (1994) Partially oxygenated sickled cells: sickle-shaped red cells found in circulating blood of patients with sickle cell disease. Proc. Natl. Acd. Sci. USA. 91:12589.
9. Baldwin, J., and Chothia, C. (1979) Haemoglobin: the structural changes related to ligand binding and its allosteric mechanism, *J. Mol. Biol.* 129, 175.

10. Ballas, S. K. (1999) Complications of sickle cell anemia in adults: guidelines for effective management. *Clev. Clin. J. Med.*, 66, 48.
11. Beddell, C. R., Goodford, P. J., Kneen, G., White, R. D., and Wilkinson, S., et al. (1984) Substituted benzaldehydes designed to increase the oxygen affinity of human haemoglobin and inhibit the sickling of sickled erythrocytes, *Br. J. Pharmacol.* 82, 397.
12. Boyiri, T., Safo, M. K., Danso Danquah, R., Kister, J., Poyart, C., and Abraham, D. J. (1995) Bisaldehyde allosteric effectors as molecular ratchets and probes, *Biochemistry* 34, 15021.
13. Brunger, A. T., Adams, P. D., Clore, G. M., DeLano, W. L., Gros, P., and Grosse-Kunstleve, R. W., et al. (1998) Crystallography & NMR system: a new software suite for macromolecular structure determination, *Acta Crystallogr.* D54, 905.
14. Bunn, H. F., and Forget, G. B. (1986) *Hemoglobin: Molecular, Genetic and Clinical Aspects*, p 462, W. B. Saunders company.
15. Cambillau, C., and Horjales, E. (1987) TOM: A Frodo subpackage for protein-ligand fitting with interactive energy minimization, *J. Mol. Graph.* 5, 174.
16. Doyle, M. L., Lew, G., Turner, G. J., Rucknagel, D., and Ackers, G. K. (1992) Regulation of oxygen affinity by quaternary enhancement: Does hemoglobin Ypsilanti represent an allosteric intermediate? *Proteins: Structure, Function, and Genetics* 14, 351.
17. Edelstein, S. J. Chapter 25, Sickle Cell Anemia In Ann. Reports in Med. Chem. Bailey, D. M., Ed.; Academic Press, Inc. 20, 247, (1985).
18. Fitzharris, P., McLean, A. E., Sparks, R. G., Weatherley, B. C., White, R. D., and Wootton, R. (1985) The effects in volunteers of BW12C, a compound designed to left-shift the blood-oxygen saturation curve, *Br. J. Clin. Pharmacol.* 19, 471.
19. Hijiya, N., Horiuchi, K., and Asakura, T. (1991) Morphology of sickle cells produced in solutions of varying osmolarities, *J. Lab. Clin. Med.* 117, 60
20. Hillery, C. A. (1998) Potential therapeutic approaches for the treatment of vaso-occlusion in sickle cell disease. *Curr. Opin. Hematol.*, 5, 151.
21. Ingram, V. M. (1956) A specific chemical difference between the globins of normal human and sickle-cell anaemia haemoglobin, *Nature* 178, 792.
22. Janin J, and Wodak S. J. (1993) The quaternary structure of carbonmonoxy Hb Ypsilanti, *Proteins* 15, 1.
23. Janzowski, C., Glaab, V., Samimi, E., Schlatter, J., and Eisenbrand, G. (2000) 5-Hydroxymethylfurfural: assessment of mutagenicity, DNA-damaging potential and reactivity towards cellular glutathione, *Food Chem. Toxicol.* 38, 801.
24. Johnson, R. M, Feo, C. J., Nossal, M. and Dobo, I. (1985) Evaluation of covalent antisickling compounds by PO2 scan ektacytometry, Blood 66, 432.
25. Johnson, F. L. (1985) Bone marrow transplantation in the treatment of sickle cell anemia. *Am. J. Pediatr. Hematol. Oncol.* 7, 254.
26. Mehanna, A. S. Sickle cell anemia and antisickling agents then and now. (2001) *Curr. Med. Chem.* 8, 79.
27. Monod, J., Wyman, J., and Changeux, J.-P. (1965) On the nature of allosteric transitions: A plausible model, *J. Mol. Biol.* 12, 88.
28. Mueser, T. M., Rogers, P. H., and Arnone, A. (2000) Interface sliding as illustrated by the multiple quaternary structures of liganded hemoglobin, *Biochemistry* 39, 15353.
29. Navaza, J. (1994) AMoRe: an automated package for molecular replacement, *Acta Crystallogr.* D50, 157.
30. Olivieri, N. F., Weatherall, D. J. (1998). The therapeutic reactivation of fetal haemoglobin. *Hum. Mol. Genet.* 7, 1655.
31. Orringer, E. P., Berkwitz, L. R. (1986) In Approaches to the therapy of sickle cell anemia, Beuzard, Y.; Charache, S., Galacteros, F., Eds.; Les Edition Inserum: Paris, 141, 301.
32. Orringer, E. P., Binder, E. A., Thomas, R. P., Blythe, D. S., and Bustrack, J. A., et al. (1988) Phase I study of BW12C in sickle cell disease (SCD) patients not in crises, *Blood*, 72, 69, (suppl).
33. Pauling, L., Itano, H. A., Singer, S. J., and Wells, I. C. (1949) Sickle Cell Anemia, a Molecular Disease, *Science* 110, 543.
34. Park, S., Hayes, B. L., Marankan, F., Mulhearn, D. C., Wanna, L., Mesecar, A. D., Santarsiero, B. D., Johnson, M. E., and Venton, D. L. (2003) Regioselective covalent modification of hemoglobin in search of antisickling agents, *J. Med. Chem.* 46, 936.
35. Perutz, M. F. (1968) Preparation of Hb crystals, *J. Crystal Growth* 2, 54.
36. Perutz, M. F. (1970) Stereochemistry of cooperative effects in hemoglobin, *Nature* 228, 726–734.
37. Reeves, R. B. (1980) The effect of temperature on the oxygen equilibrium curve of human blood, *Resir. Physiol.*, 42, 317.
38. Safo, M. K., and Abraham, D. J. (2003) in Ronald L. Nagel, Ed., Methods in Molecular Medicine: Hemoglobin Disorders, Molecular Methods and Protocols, Vol. 82, p. 1. Humana Press Inc, Totowa, N.J.
39. Silva, M. M., Rogers, P. H., and Arnone, A. (1992) A third quaternary structure of human Hb at 1.7 Å resolution, *J. Biol. Chem.* 267, 17248.
40. Smith, F. R., Lattman, E. E., and Carter, C. W. R. (1991) The mutation β99 Asp-Tyr stabilizes a new composite quaternary state of human Hb, *Proteins* 10, 81.
41. Srinivasan, R., and Rose, G. D. (1994) The T-to-R transformation in Hb: a re-valuation, *Proc Natl Acad Sci USA* 91, 11113.
42. Zuagg, R. H, Walder, J. A, and Klotz, I. M. (1977) Schiff Base Adducts of Hemoglobin Modifications that inhibit erythrocyte sickling, *J. Biol. Chem.* 252, 8542.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. A method for treating sickle cell disease in a patient in need thereof, comprising the step of administering to said patient a compound of the formula:

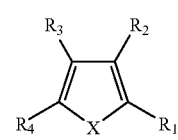

where

R1 is CHO or a thiozolidine group of the following formula:

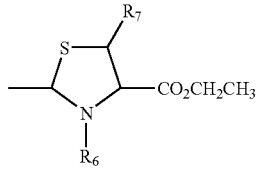

R2, R3 and R4 are the same or different and selected from the group consisting of H, OH, alkyl, halogen and hydroxy-alkyl; R6 and R7=H;

X=O or S;

and wherein said compound is administered in sufficient amount to said patient to ameliorate sickle cell disease, with the proviso that R2,R3 and R4 cannot be H or alkyl at the same time when R1 is CHO and X is O.

2. The method of claim 1, wherein R2 and R3=H; R4 is H, alkyl or hydroxyalkyl; and the general formula of the compound is:

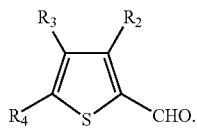

3. The method of claim 1, wherein said compound is of the formula:

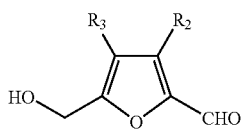

where R2 and R3=H.

4. The method of claim 1, wherein said compound is of the formula:

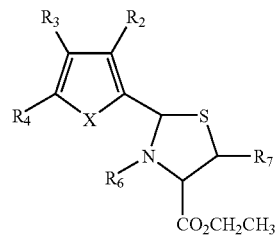

where
R2, R3=H; R4 is H, alkyl or hydroxy-alkyl; R6 and R7=H; and X=O.

5. The method of claim 4, wherein said compound is of the formula:

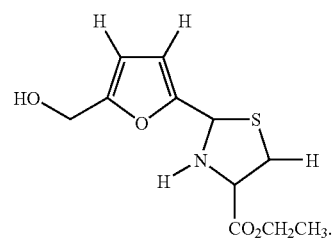

6. The method of claim 1, wherein said compound is selected from the group consisting of a compound of the formula:

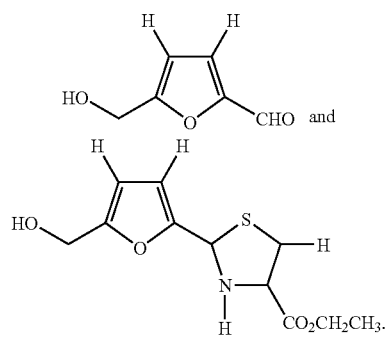

* * * * *

UNITED STATES PATENT AND TRADEMARK OFFICE
CERTIFICATE OF CORRECTION

PATENT NO. : 7,160,910 B2  Page 1 of 1
APPLICATION NO. : 10/725935
DATED : January 9, 2007
INVENTOR(S) : Martin K. Safo et al.

It is certified that error appears in the above-identified patent and that said Letters Patent is hereby corrected as shown below:

In the Specification

At column 1, lines 1-6, please replace [[This invention was made using funds from grants from the National Institutes of Health having grant numbers NIH K01HL004367 and NIH RO1HL32793. The United States government may have certain rights in this invention.]] with --This invention was made with government support under contract numbers K01 HL004367, K01 HL032793, and R01 HL065715 awarded by the National Institutes of Health. The government has certain rights in the invention.--.

Signed and Sealed this
Fifteenth Day of July, 2014

Michelle K. Lee
*Deputy Director of the United States Patent and Trademark Office*